United States Patent
Roe et al.

(10) Patent No.: US 9,011,402 B2
(45) Date of Patent: Apr. 21, 2015

(54) DISPOSABLE ABSORBENT INSERT FOR TWO-PIECE WEARABLE ABSORBENT ARTICLE

(75) Inventors: Donald Carroll Roe, West Chester, OH (US); Elaine Mary Wiggins, Fairfield Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 880 days.

(21) Appl. No.: 12/687,507

(22) Filed: Jan. 14, 2010

(65) Prior Publication Data
US 2010/0179496 A1    Jul. 15, 2010

Related U.S. Application Data

(60) Provisional application No. 61/144,866, filed on Jan. 15, 2009.

(51) Int. Cl.
*A61F 13/505*    (2006.01)
*A61F 13/74*    (2006.01)
(Continued)

(52) U.S. Cl.
CPC ............. *A61F 13/74* (2013.01); *A61F 13/4752* (2013.01); *A61F 13/49004* (2013.01); *A61F 13/505* (2013.01); *A61F 2013/51449* (2013.01)

(58) Field of Classification Search
CPC .................. A61F 13/505; A61F 2013/530547; A61F 13/74
USPC .......................... 604/385.14, 385.15, 386–399
See application file for complete search history.

(56) References Cited

U.S. PATENT DOCUMENTS 2,119,610 A * 6/1938 Tasker .......................... 604/401
2,530,647 A    11/1950 Buchler
(Continued)

FOREIGN PATENT DOCUMENTS

AU        642 386      10/1993
CA      2 103 537       2/1995
(Continued)

OTHER PUBLICATIONS www.gdiapers.com—Web pages dated Nov. 23, 2009.
(Continued)

*Primary Examiner* — Tan-Uyen (Jackie) T Ho
*Assistant Examiner* — Peter S Vasat
(74) *Attorney, Agent, or Firm* — Christian M. Best; William E. Gallagher

(57) ABSTRACT

A wearable absorbent article having features for the containment and absorption of bodily exudates. The article may comprise an outer cover and an absorbent insert. The outer cover may be formed of durable or semi-durable materials and be launderable. The insert may be disposable. The insert may have containment and absorption features that prevent soiling of the outer cover by the wearer's exudates, so that the outer cover may be reused after an exudation event and change of inserts. The insert and/or the outer cover may have features to enhance containment, absorption, economy of materials and/or fit that make them asymmetric about their respective lateral axes, and may have features that direct a user to install the insert and/or the outer cover with correct front-rear orientation relative the wearer. Articles of commerce including packages of outer covers and/or inserts in varying combinations of numbers and features are also described.

16 Claims, 20 Drawing Sheets

(51) Int. Cl.
*A61F 13/475* (2006.01)
*A61F 13/49* (2006.01)
*A61F 13/514* (2006.01)

(56) References Cited

U.S. PATENT DOCUMENTS

| | | |
|---|---|---|
| 2,688,328 A | 9/1954 | Marcus |
| 2,793,642 A | 5/1957 | Andruhovici |
| 3,077,193 A | 2/1963 | Mann |
| 3,496,259 A | 2/1970 | Guenther |
| 3,560,292 A | 2/1971 | Butter |
| 3,719,736 A | 3/1973 | Woodruff |
| 3,735,424 A | 5/1973 | Maggio et al. |
| 3,860,003 A | 1/1975 | Buell |
| 3,911,173 A | 10/1975 | Sprague, Jr. |
| 3,926,189 A | 12/1975 | Taylor |
| 3,929,135 A | 12/1975 | Thompson |
| 3,955,575 A | 5/1976 | Okuda |
| 4,022,210 A | 5/1977 | Glassman |
| 4,072,150 A | 2/1978 | Glassman |
| 4,081,301 A | 3/1978 | Buell |
| 4,116,892 A | 9/1978 | Schwarz |
| 4,195,634 A | 4/1980 | DiSalvo et al. |
| 4,223,059 A | 9/1980 | Schwarz |
| 4,265,245 A | 5/1981 | Glassman |
| 4,284,454 A | 8/1981 | Joa |
| 4,324,246 A | 4/1982 | Mullane et al. |
| 4,326,302 A | 4/1982 | Lowe et al. |
| 4,338,939 A | 7/1982 | Daville |
| 4,342,314 A | 8/1982 | Radel et al. |
| 4,352,356 A | 10/1982 | Tong |
| 4,438,167 A | 3/1984 | Schwarz |
| 4,463,045 A | 7/1984 | Ahr et al. |
| 4,475,912 A | 10/1984 | Coates |
| 4,496,360 A | 1/1985 | Joffe et al. |
| 4,573,986 A | 3/1986 | Minetola et al. |
| 4,578,073 A | 3/1986 | Dysart et al. |
| 4,579,556 A | 4/1986 | Mcfarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,615,695 A | 10/1986 | Cooper |
| 4,625,245 A | 11/1986 | White |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,710,187 A | 12/1987 | Boland et al. |
| 4,747,846 A | 5/1988 | Boland et al. |
| 4,756,709 A | 7/1988 | Stevens |
| 4,770,656 A | 9/1988 | Proxmire et al. |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,955,880 A | 9/1990 | Rodriquez |
| 4,961,736 A | 10/1990 | McCloud |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | DesMarais et al. |
| 5,261,901 A | 11/1993 | Guay |
| 5,269,775 A | 12/1993 | Freeland et al. |
| 5,283,910 A | 2/1994 | Flint |
| 5,296,184 A | 3/1994 | Wu et al. |
| 5,306,267 A | 4/1994 | Hahn et al. |
| 5,342,338 A | 8/1994 | Roe |
| 5,354,597 A | 10/1994 | Capik et al. |
| 5,360,422 A | 11/1994 | Brownlee et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,458,591 A | 10/1995 | Roessler et al. |
| 5,476,457 A | 12/1995 | Roessler et al. |
| 5,509,915 A | 4/1996 | Hanson et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A | 10/1996 | Peterson |
| 5,571,096 A | 11/1996 | Dobrin et al. |
| 5,607,760 A | 3/1997 | Roe |
| 5,609,587 A | 3/1997 | Roe |
| 5,613,959 A | 3/1997 | Roessler et al. |
| 5,624,425 A | 4/1997 | Gray et al. |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kj.ae butted.rgaard et al. |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,795,348 A | 8/1998 | Roe et al. |
| 5,795,384 A | 8/1998 | Coyle et al. |
| 5,814,037 A | 9/1998 | Coates |
| 5,827,261 A | 10/1998 | Osborn et al. |
| 5,843,065 A | 12/1998 | Wyant |
| 5,843,267 A | 12/1998 | Cashaw et al. |
| H0001788 H | 2/1999 | Christon et al. |

(56) References Cited

U.S. PATENT DOCUMENTS

| | | |
|---|---|---|
| 5,865,823 A | 2/1999 | Curro |
| 5,906,603 A | 5/1999 | Roe et al. |
| 5,911,713 A | 6/1999 | Yamada et al. |
| 5,938,648 A | 8/1999 | Lavon et al. |
| 5,941,864 A | 8/1999 | Roe |
| 5,947,946 A | 9/1999 | Fisher et al. |
| 5,968,025 A | 10/1999 | Roe et al. |
| 5,984,911 A | 11/1999 | Siebers et al. |
| 6,007,528 A | 12/1999 | Osborn |
| 6,010,491 A | 1/2000 | Roe et al. |
| 6,120,487 A | 9/2000 | Ashton |
| 6,142,983 A | 11/2000 | Suprise et al. |
| 6,207,738 B1 | 3/2001 | Zuckerman et al. |
| 6,229,061 B1 | 5/2001 | Dragoo et al. |
| 6,240,569 B1 | 6/2001 | Van Gompel et al. |
| 6,251,097 B1 | 6/2001 | Kline et al. |
| 6,254,583 B1 | 7/2001 | Coates |
| 6,258,308 B1 | 7/2001 | Brady et al. |
| 6,278,037 B1 | 8/2001 | Schmidt et al. |
| 6,287,169 B1 | 9/2001 | Willms et al. |
| 6,291,039 B1 | 9/2001 | Combe et al. |
| 6,307,119 B1 | 10/2001 | Cammarota et al. |
| 6,368,444 B1 | 4/2002 | Jameson et al. |
| 6,414,215 B1 | 7/2002 | Roe |
| 6,420,627 B1 | 7/2002 | Ohnishi et al. |
| 6,423,042 B1 | 7/2002 | Sasaki |
| 6,423,043 B1 | 7/2002 | Gustafsson |
| 6,432,098 B1 | 8/2002 | Kline et al. |
| 6,468,257 B1 | 10/2002 | Ono et al. |
| 6,482,191 B1 | 11/2002 | Roe et al. |
| 6,514,362 B1 | 2/2003 | Zuckerman et al. |
| 6,526,631 B1 | 3/2003 | Alberg et al. |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,575,951 B1 * | 6/2003 | Ono et al. ............... 604/385.14 |
| 6,579,273 B2 | 6/2003 | Dupuy |
| 6,623,466 B1 * | 9/2003 | Richardson ............... 604/385.19 |
| 6,669,618 B2 | 12/2003 | Reising et al. |
| 6,680,422 B2 | 1/2004 | Roe |
| 6,709,423 B2 | 3/2004 | Herrlein et al. |
| 6,716,441 B1 | 4/2004 | Osborne et al. |
| 6,763,944 B2 | 7/2004 | Ronn et al. |
| 6,764,477 B1 | 7/2004 | Chen et al. |
| 6,764,478 B2 | 7/2004 | Ashton et al. |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,936,039 B2 | 8/2005 | Kline et al. |
| 6,964,720 B2 | 11/2005 | Schneider et al. |
| 6,966,720 B2 | 11/2005 | Moss |
| 6,980,872 B2 | 12/2005 | Kano et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,166,095 B1 | 1/2007 | Coates |
| 7,211,531 B2 | 5/2007 | Schneider |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,344,526 B2 | 3/2008 | Yang et al. |
| 7,387,620 B2 | 6/2008 | Watanabe et al. |
| 7,407,468 B2 | 8/2008 | Reising et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Franke et al. |
| 7,537,587 B2 | 5/2009 | Carstens |
| 7,576,019 B2 | 8/2009 | Bond et al. |
| 7,629,501 B2 | 12/2009 | Labit et al. |
| 7,666,175 B2 | 2/2010 | Trennepohl |
| 7,695,463 B2 | 4/2010 | Lavon et al. |
| 7,771,406 B2 | 8/2010 | Mueller et al. |
| 7,771,408 B2 | 8/2010 | Mueller et al. |
| 7,776,770 B2 | 8/2010 | Wang et al. |
| 7,776,771 B2 | 8/2010 | Autran et al. |
| 7,820,875 B2 | 10/2010 | Roe et al. |
| 7,833,211 B2 | 11/2010 | Mansfield |
| 7,842,627 B2 | 11/2010 | Gao et al. |
| 7,872,169 B2 | 1/2011 | Ruiz et al. |
| 7,875,014 B2 | 1/2011 | Hendren et al. |
| 7,887,527 B2 | 2/2011 | Hayashi et al. |
| 7,914,507 B1 | 3/2011 | Magee |
| 7,993,322 B2 | 8/2011 | Brud et al. |
| 8,118,801 B2 | 2/2012 | Macura et al. |
| 8,158,043 B2 | 4/2012 | Gibson et al. |
| 8,262,635 B2 | 9/2012 | Labit et al. |
| 2002/0010452 A1 | 1/2002 | Dupuy |
| 2002/0035747 A1 | 3/2002 | Kusibojoska et al. |
| 2002/0128619 A1 | 9/2002 | Carlbark et al. |
| 2002/0143316 A1 | 10/2002 | Sherrod et al. |
| 2003/0088220 A1 | 5/2003 | Molander et al. |
| 2003/0091807 A1 | 5/2003 | Desai et al. |
| 2003/0114805 A1 | 6/2003 | Rainville-Lonn et al. |
| 2003/0125701 A1 | 7/2003 | Widlund |
| 2003/0163104 A1 | 8/2003 | Tears et al. |
| 2003/0233082 A1 | 12/2003 | Kline et al. |
| 2004/0023771 A1 | 2/2004 | Reising et al. |
| 2004/0127867 A1 | 7/2004 | Odorzynski et al. |
| 2005/0033258 A1 | 2/2005 | Suzuki et al. |
| 2005/0096624 A1 | 5/2005 | Hoshino et al. |
| 2005/0148974 A1 | 7/2005 | Datta et al. |
| 2005/0164587 A1 | 7/2005 | Melik et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2006/0035055 A1 | 2/2006 | Schneider et al. |
| 2006/0047260 A1 | 3/2006 | Ashton et al. |
| 2006/0058766 A1 | 3/2006 | Mueller et al. |
| 2006/0069372 A1 | 3/2006 | Chakravarty et al. |
| 2006/0087053 A1 | 4/2006 | O'Donnell et al. |
| 2006/0095012 A1 | 5/2006 | Cohen |
| 2006/0107505 A1 | 5/2006 | Desai et al. |
| 2006/0129114 A1 | 6/2006 | Mason et al. |
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1 | 10/2006 | LaVon |
| 2006/0247599 A1 | 11/2006 | Mullen et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 | 11/2006 | Carstens |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0123834 A1 | 5/2007 | McDowall et al. |

(56) References Cited

U.S. PATENT DOCUMENTS

| | | |
|---|---|---|
| 2007/0142798 A1 | 6/2007 | Goodlander et al. |
| 2007/0142816 A1 | 6/2007 | Carstens |
| 2007/0191806 A1 | 8/2007 | Mueller et al. |
| 2007/0203301 A1* | 8/2007 | Autran et al. |
| 2007/0239130 A1 | 10/2007 | Trennepohl |
| 2007/0249254 A1 | 10/2007 | Mansfield |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdon et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Mueller et al. |
| 2008/0045917 A1 | 2/2008 | Autran et al. |
| 2008/0081854 A1 | 4/2008 | Wang et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0119816 A1 | 5/2008 | Carstens |
| 2008/0125739 A1 | 5/2008 | Lodge et al. |
| 2008/0188822 A1 | 8/2008 | Lodge et al. |
| 2008/0224351 A1 | 9/2008 | Curro et al. |
| 2008/0287983 A1 | 11/2008 | Smith et al. |
| 2008/0312617 A1 | 12/2008 | Hundorf et al. |
| 2008/0312618 A1* | 12/2008 | Hundorf et al. ............... 604/366 |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0069722 A1 | 3/2009 | Flaction et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0127742 A1 | 5/2009 | Qureshi et al. |
| 2009/0216209 A1 | 8/2009 | Ekstrom |
| 2010/0004616 A1 | 1/2010 | Nakamura et al. |
| 2010/0005570 A1 | 1/2010 | Rachman |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe et al. |
| 2010/0201024 A1 | 8/2010 | Gibson et al. |
| 2010/0331803 A1 | 12/2010 | Saito |
| 2011/0137277 A1 | 6/2011 | Hough et al. |
| 2012/0049404 A1 | 3/2012 | Gibson et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |

FOREIGN PATENT DOCUMENTS

| | | |
|---|---|---|
| CA | 2221209 A1 | 11/1996 |
| CA | 2 365 577 A1 | 6/2003 |
| DE | 103 03 903 A1 | 11/2003 |
| EP | 0 023 804 | 2/1981 |
| EP | 0 187 726 | 7/1986 |
| EP | 319314 A2 | 6/1989 |
| EP | 0667136 | 8/1995 |
| EP | 549988 B1 | 6/1998 |
| EP | 796069 B1 | 8/2000 |
| EP | 763353 B1 | 6/2002 |
| FR | 2532337 | 3/1984 |
| GB | 112638 | 1/1918 |
| GB | 2 440 314 A | 1/2008 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 62-110903 | 7/1987 |
| JP | 03-091325 | 1/1990 |
| JP | 4-7792 | 11/1990 |
| JP | 06-178795 | 1/1993 |
| JP | 2001-346826 | 12/2001 |
| JP | 2002-325786 | 11/2002 |
| JP | 2003-038564 | 2/2003 |
| JP | 2003-093438 | 4/2003 |
| JP | 2003-190213 | 7/2003 |
| JP | 2004-261332 | 9/2004 |
| JP | 2005-6827 | 1/2005 |
| JP | 2005-111119 | 4/2005 |
| JP | 2005-118533 | 5/2005 |
| JP | 3109189 | 5/2005 |
| JP | 2007/244506 | 3/2006 |
| JP | 2008-237231 | 10/2008 |
| JP | 2009-153736 | 7/2009 |
| JP | 47-40720 | 8/2011 |
| WO | WO-90/08524 | 8/1990 |
| WO | WO-91/16871 A1 | 11/1991 |
| WO | WO-92/01431 A1 | 2/1992 |
| WO | WO-92/15444 | 9/1992 |
| WO | WO-94/15563 A1 | 7/1994 |
| WO | WO-94/15663 A1 | 7/1994 |
| WO | WO-95/10992 | 4/1995 |
| WO | WO-95/10992 A1 | 4/1995 |
| WO | WO-95/16746 A1 | 6/1995 |
| WO | WO-96/17572 A1 | 6/1996 |
| WO | WO-96/24319 | 8/1996 |
| WO | WO-96/32912 A1 | 10/1996 |
| WO | WO-00/65348 A1 | 11/2000 |
| WO | WO-02/066086 | 8/2002 |
| WO | WO-2004/060229 A2 | 7/2004 |
| WO | WO-2005/039469 | 5/2005 |
| WO | WO-2005/052052 | 6/2005 |
| WO | WO-2005/096855 | 10/2005 |
| WO | WO-2005/097031 | 10/2005 |
| WO | WO-2008/030984 A2 | 3/2008 |
| WO | WO-2008/120959 A1 | 10/2008 |
| WO | WO-2008/142634 | 11/2008 |
| WO | WO-2010/053006 | 5/2010 |
| WO | WO 2010078661 | 7/2010 |

OTHER PUBLICATIONS www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.

(56) References Cited

OTHER PUBLICATIONS

Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants.
Data Sheet, p. V-17, from "Baby Diaper Design Update—1987", publication of Marketing Technology Service, Inc., product believed to be a product of Kao Corp. sold in Japan in 1986 or 1987.
International Search Report.
U.S. Appl. No. 12/687,493, filed Jan. 14, 2010, Donald Carroll Roe et al.
U.S. Appl. No. 12/687,527, filed Jan. 14, 2010, Donald Carroll Roe et al.
U.S. Appl. No. 12/687,538, filed Jan. 14, 2010, Donald Carroll Roe et al.
U.S. Appl. No. 12/366,825, filed Feb. 5, 2009, Fredrick William Gibson et al.
U.S. Appl. No. 12/534,353, filed Aug. 3, 2009, Khalid Qureshi et al.
U.S. Appl. No. 12/687,425, filed Jan. 14, 2010, Donald Carroll Roe et al.
U.S. Appl. No. 12/785,152, filed May 21, 2010, Donald Carroll Roe et al.
U.S. Appl. No. 12/785,166, filed May 21, 2010, Donald Carroll Roe et al.
U.S. Appl. No. 12/785,181, filed May 21, 2010, Donald Carroll Roe et al.
U.S. Appl. No. 12/841,553, filed Jul. 22, 2010, Donald Carroll Roe et al.
International Search Report/Written Opinion, PCT/US2010/021015, mailed Jun. 14, 2010, 12 pages.
All Office Actions, U.S. Appl. No. 12/534,353.
All Office Actions, U.S. Appl. No. 12/687,425.
All Office Actions, U.S. Appl. No. 12/841,553.
All Office Actions, U.S. Appl. No. 12/687,437.
All Office Actions, U.S. Appl. No. 13/183,952.
All Office Actions, U.S. Appl. No. 12/687,493.
All Office Actions, U.S. Appl. No. 12/687,527.
All Office Actions, U.S. Appl. No. 12/687,538.
All Office Actions, U.S. Appl. No. 12/687,554.
All Office Actions, U.S. Appl. No. 12/687,444.
All Office Actions, U.S. Appl. No. 12/785,152.
All Office Actions, U.S. Appl. No. 12/785,166.
All Office Actions, U.S. Appl. No. 12/785,181.
ISR and Written Opinion PCT/US2010/021015, date of mailing Jun. 14, 2010.
All Office Actions, Responses and Claims, U.S. Appl. No. 13/183,952.
All Office Actions, Responses and Claims, U.S. Appl. No. 12/687,437.
All Office Actions, Responses and Claims, U.S. Appl. No. 12/687,493.
All Office Actions, Responses and Claims, U.S. Appl. No. 12/687,527.
All Office Actions, Responses and Claims, U.S. Appl. No. 12/687,538.
All Office Actions, Responses and Claims, U.S. Appl. No. 12/687,554.
All Office Actions, Responses and Claims, U.S. Appl. No. 12/687,444.
All Office Actions, Responses and Claims, U.S. Appl. No. 12/785,152.
All Office Actions, Responses and Claims, U.S. Appl. No. 12/785,166.
All Office Actions, Responses and Claims, U.S. Appl. No. 12/785,181.
All Office Actions, Responses and Claims, U.S. Appl. No. 14/053,014.
All Office Actions, Responses and Claims, U.S. Appl. No. 12/841,553.
All Office Actions, Responses and Claims, U.S. Appl. No. 12/841,467.
All Office Actions, Responses and Claims, U.S. Appl. No. 13/859,015.
All Office Actions, Responses and Claims, U.S. Appl. No. 12/841,600.
All Office Actions, Responses and Claims, U.S. Appl. No. 14/014,440.
All Office Actions, Responses and Claims, U.S. Appl. No. 13/537,626.

\* cited by examiner

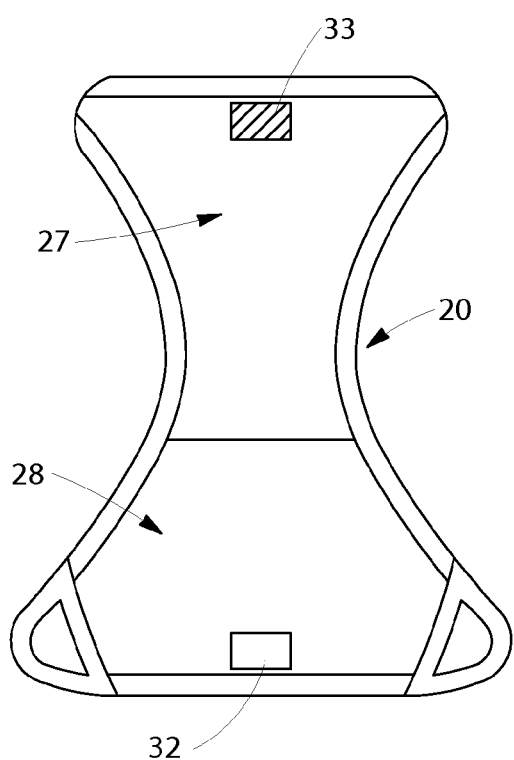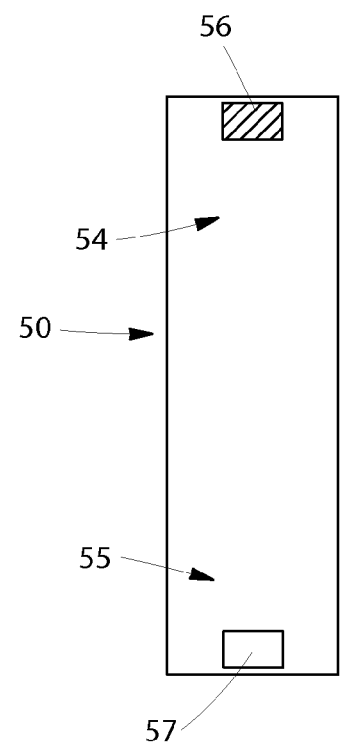
Fig. 2K
Fig. 2L

DISPOSABLE ABSORBENT INSERT FOR TWO-PIECE WEARABLE ABSORBENT ARTICLE

CROSS REFERENCE TO RELATED APPLICATION

To the extent allowable, this application claims the benefit of the filing date of U.S. Provisional Application No. 61/144,866, filed Jan. 15, 2009, the substance of which is incorporated herein by reference.

FIELD OF THE INVENTION

The present invention relates generally to the field of diapers and other wearable absorbent articles having features for the containment and absorption of bodily exudates, and more particularly, to such articles having disposable absorbent inserts and reusable outer covers.

BACKGROUND OF THE INVENTION

It is likely that reusable diapers made of cloth have been in use since the invention of cloth. Reusable cloth diapers, however, present difficulties relating to sanitation needs, in handling, laundering and effectively sanitizing soiled diapers for re-use. Reusable cloth diapers also may be relatively unreliable with respect to containing bodily exudates (i.e., they may tend to leak). Because a wet cloth diaper may be in direct contact with the skin, unless wetness is quickly detected and the wet diaper removed, it may promote over-hydration of the wearer's skin, which makes the skin vulnerable to diaper rash.

The introduction of disposable diapers in relatively recent times has mitigated these disadvantages for many. Generally, upon removal from a wearer, a soiled disposable diaper need not be emptied, laundered or handled to any significant extent, but rather, may be discarded as is. Any soiled areas of the wearer's body may then be cleaned, and a clean new disposable diaper may be placed on the wearer as necessary. Many current disposable diapers have structures that make them relatively more effective at containing exudates than traditional cloth diapers. Many have structures and materials that make them relatively more effective at conveying and storing liquid exudates away from the wearer's skin. Some have features that enable them to "breathe", thereby reducing humidity inside the diaper, and some even include skin care compositions that are transferred to the skin when the diaper is worn. Such features may reduce the likelihood and/or extent of skin over-hydration and otherwise promote or help maintain skin health.

For economic reasons, currently most disposable diapers are made of substantial proportions of materials derived from petroleum, such as polypropylene and/or polyethylene. These materials often appear in the form of spun fibers forming cloth-like nonwoven web materials, or alternatively or in addition, films.

In recent years concerns have arisen concerning the "environmental footprint" of human activities of all kinds. The manufacture and use of diapers is no exception, particularly in view of the growing human population, i.e., the growing number of babies. One view seems to be that use of disposable diapers is detrimental to the environment because the materials of which they are typically made may be derived from non-renewable resources and require substantial amounts of energy in their manufacture. Additionally, because disposable diapers typically are not re-used or recycled, their use may be deemed by some to be unsatisfactorily taxing upon disposal facilities such as landfills. If the alternative is reusable cloth diapers, however, another view seems to be that the increased use of energy (e.g., for operating equipment, heating laundry water, and treating wastewater) and chemicals (e.g., detergents and water treatment agents), necessary for laundering soiled diapers at the rate they are typically used, and treating the associated wastewater, present their own set of stresses on the environment. As may be appreciated, analysis concerning which alternative is more "environmentally friendly" is complicated, and undisputed conclusions either way do not yet appear to exist.

Regardless of which alternative one may believe is more environmentally friendly, however, it appears that in developed nations, today's disposable diapers are generally favored over reusable cloth diapers among caregivers of babies and young children. This is probably attributable to the advantages of reducing or eliminating the unpleasantness, sanitary concerns, and extra work and/or expense associated with handling and laundering soiled reusable cloth diapers, better containment of exudates, and effectiveness at promoting and/or helping maintain skin health.

Manufacture of wholly disposable diapers is generally considered a capital-intensive business. This is a consequence of the complex machinery required to produce product from incoming material streams at economically-feasible production rates, which often exceed 450 or more articles per manufacturing line, per minute. Any innovation which has the potential to simplify the process or the equipment required, or reduce material costs, has the corresponding potential to reduce per-article costs for the manufacturer and the consumer.

Several designs of diapers that include a reusable cloth outer cover and either a reusable or a disposable absorbent insert have been manufactured and marketed. However, for the user, these designs have still presented at least some of the disadvantages of traditional cloth diapers, while not providing some of the advantages available from current disposable diaper designs.

In view of the concerns set forth above, it would be advantageous if a wearable absorbent article were available that provides advantages afforded by both disposable and reusable diapers, while reducing the respective disadvantages of these alternatives. It also would be advantageous if a construction were provided that could simplify manufacturing processes and/or reduce costs.

BRIEF DESCRIPTION OF TILE DRAWINGS

FIG. 2K is a plan view of an outer cover opened and laid flat, inner surface facing the viewer;

FIG. 2L is a plan view of an insert opened and laid flat, outer (garment-facing) surface facing the viewer;

DETAILED DESCRIPTION OF THE INVENTION

Definitions

Figure 1:
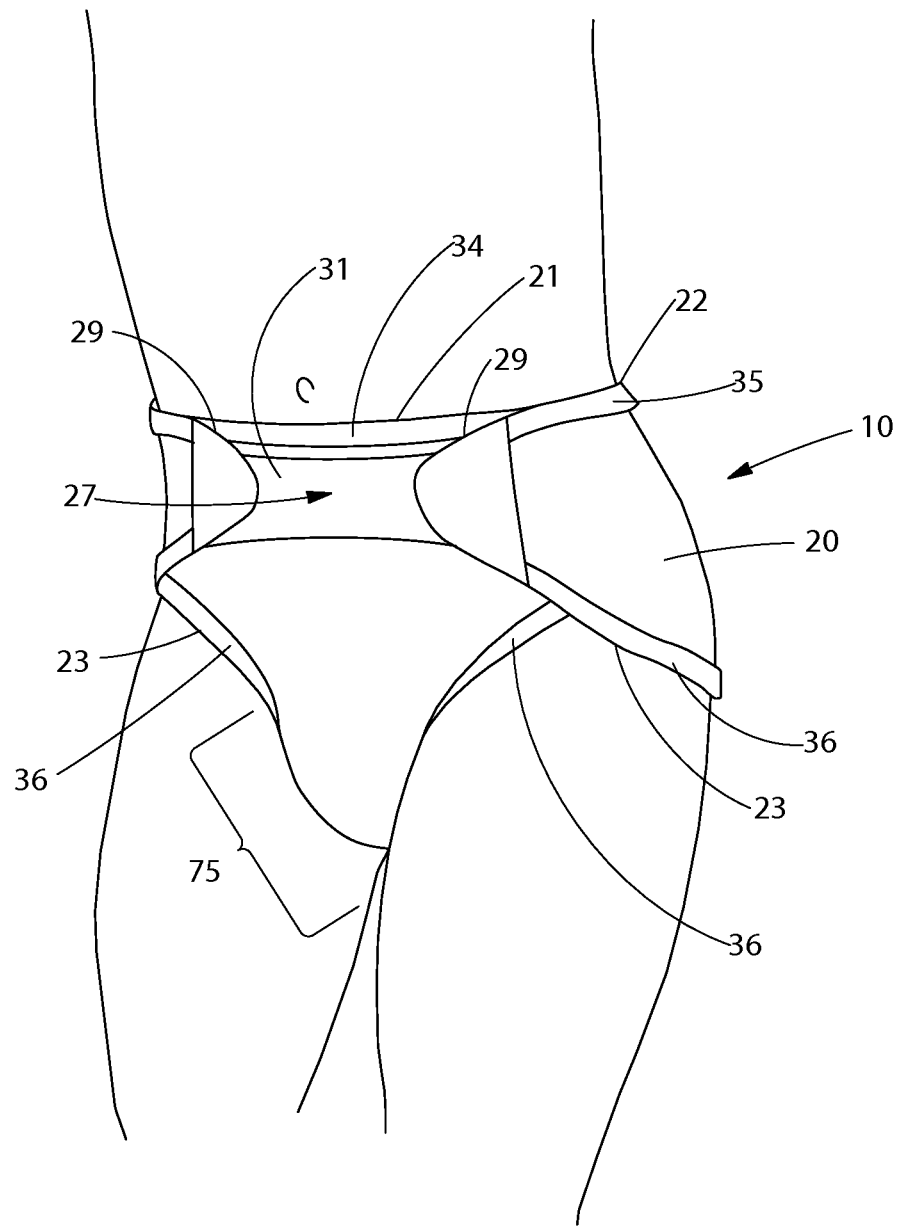
FIG. 1 is a perspective view of a wearable absorbent article as it might appear being worn by a wearer about the lower torso.

For purposes of this description, the following terms have the meanings set forth:

"Absorbent insert" and "insert" mean a component of a wearable absorbent article that is adapted to contain and/or absorb urine, feces, menses or any combination thereof, and is adapted to be installable and removable as a modular unit, from an outer cover. Herein, an absorbent insert may also be referred to as an "absorbent assembly". The terms "absorbent insert," "insert" and "absorbent assembly" may be used interchangeably herein.

"Chassis" means a component of a wearable absorbent article that is adapted to be worn about the lower torso of a wearer, and is adapted to support an absorbent insert and hold the insert next to the wearer's body. Herein, a chassis may also be referred to as an "outer cover". The terms "outer cover" and "chassis" are interchangeable for purposes herein.

"Disposable", when referring to an absorbent insert, means that the absorbent insert is not adapted or intended to be effectively sanitarily laundered in an ordinary household laundering process and ordinary household equipment, and thereby is ordinarily unsuitable for sanitary and effective reuse so as to provide as-new intended functions and performance, following soiling by exudates and removal from an outer cover. By way of non-limiting examples, effective laundering may be frustrated or prevented, causing the insert to be disposable, by inclusion of materials and/or construction: that do not retain their substantial as-new physical shape or structure through ordinary household laundering and drying so as to be effective as-new in reuse; that absorb aqueous liquids and cannot be sufficiently dried/dehydrated in ordinary household drying equipment and ordinary drying cycles so as to be effective as-new in reuse; that dissolve or substantially degrade in ordinary household laundering or drying, causing the insert to be substantially damaged or rendered useless; and/or that cannot be effectively cleaned of exudate material through ordinary laundering, so as to be sanitary and otherwise acceptable for re-use.

"Fastener component" means any component of a system that effects removable fastening, attachment or holding of a first structure to a second structure. The system may have a single fastener component, for example, an adhesive patch on the first structure adapted to adhere to one or more types of surfaces on the second structure, or a hook, or patch of hooks on the first structure, adapted to catch on one or more types of surfaces on the second structure. By way of further example, any structure such as a pocket, strap, hook, buckle, etc. on a first structure adapted to capture and retain, in whole or in part, the second structure, is a "fastener component" as used herein. The system also may comprise two or more fastener components, for example, respective components of a hook-and-loop fastening system such as VELCRO), respective surfaces having a cohesive material applied thereto; male and female snap fastener components, a button and button hole, slot or loop, other fastenably cooperating elements, etc. Other examples of fastener components include zipper components, "zip lock" engaging components, loops, posts, pockets, bands or straps, microfasteners, macrofasteners, and fastener components such as described in U.S. Pat. Nos. 6,936, 039; 6,893,388; 6,669,618; 6,432,098; and 6,251,097, and U.S. Published Applications, Pub. Nos. 2005/0234419; 2005/0215971; 2005/0215970; 2005/0130821; 2004/0023771; 2003/0233082; 2003/0119641; 2003/0088220; and 2002/0169431.

"Lateral" (and forms thereof), with respect to a wearer, means along a direction generally transverse or across the direction extending from the front to the rear of the wearer, or vice versa. With respect to a component of a wearable absorbent article, "lateral" (and forms thereof), means along a direction generally transverse or across the direction extending along the component as it would be properly situated on a wearer, from the front to the rear of the wearer, or vice versa.

"Longitudinal" (and forms thereof), with respect to a wearer, means along a direction generally extending from the front to the rear of the wearer, or vice versa. With respect to a component of a wearable absorbent article, "longitudinal" (and forms thereof), means along a direction generally extending along the component as it would be properly situated on a wearer, from the front to the rear of the wearer, or vice versa.

"Outer cover" means a component of a wearable absorbent article that is adapted to be worn about the lower torso of a wearer, and is adapted to support an absorbent insert and hold the insert next to the wearer's body. Herein, an outer cover may also be referred to as a "chassis". The terms "outer cover" and "chassis" are interchangeable for purposes herein.

"Reusable", when referring to an outer cover, means an outer cover that is adapted to permit removal of at least a first insert, and replacement thereof with at least a second insert, without substantial destruction of any components of the outer cover that are necessary to provide the substantial as-new functionality of the outer cover, and without the necessity of any repair or reconstruction following such insert replacement.

"Use," with respect to an outer cover, means one event of the wearing of the outer cover until the time an absorbent insert is replaced.

"User" means a caregiver or other person who may apply a wearable absorbent article to a wearer. Where the wearer is capable of donning the wearable absorbent article him/herself, the wearer is also a "user".

"Wearer" means a person who may wear a wearable absorbent article as described herein.

"Wearable absorbent article" means any article designed to be worn about the lower torso and to contain and/or absorb urine, feces, menses or any combination thereof. "Wearable absorbent article" includes but is not limited to baby or children's diapers (of the "tape"-fastenable, otherwise fastenable, "pull-up" or any other variety), training pants and adult incontinence pants, briefs and the like.

Two-Piece Wearable Absorbent Articles

FIG. 1 depicts an example of a wearable absorbent article 10 having certain features, as it might appear while being worn by a wearer. Wearable absorbent article 10 may include an outer cover 20, having front waist edge 21, rear waist edge 22, and a pair of leg opening edges 23.

Figure 2A:
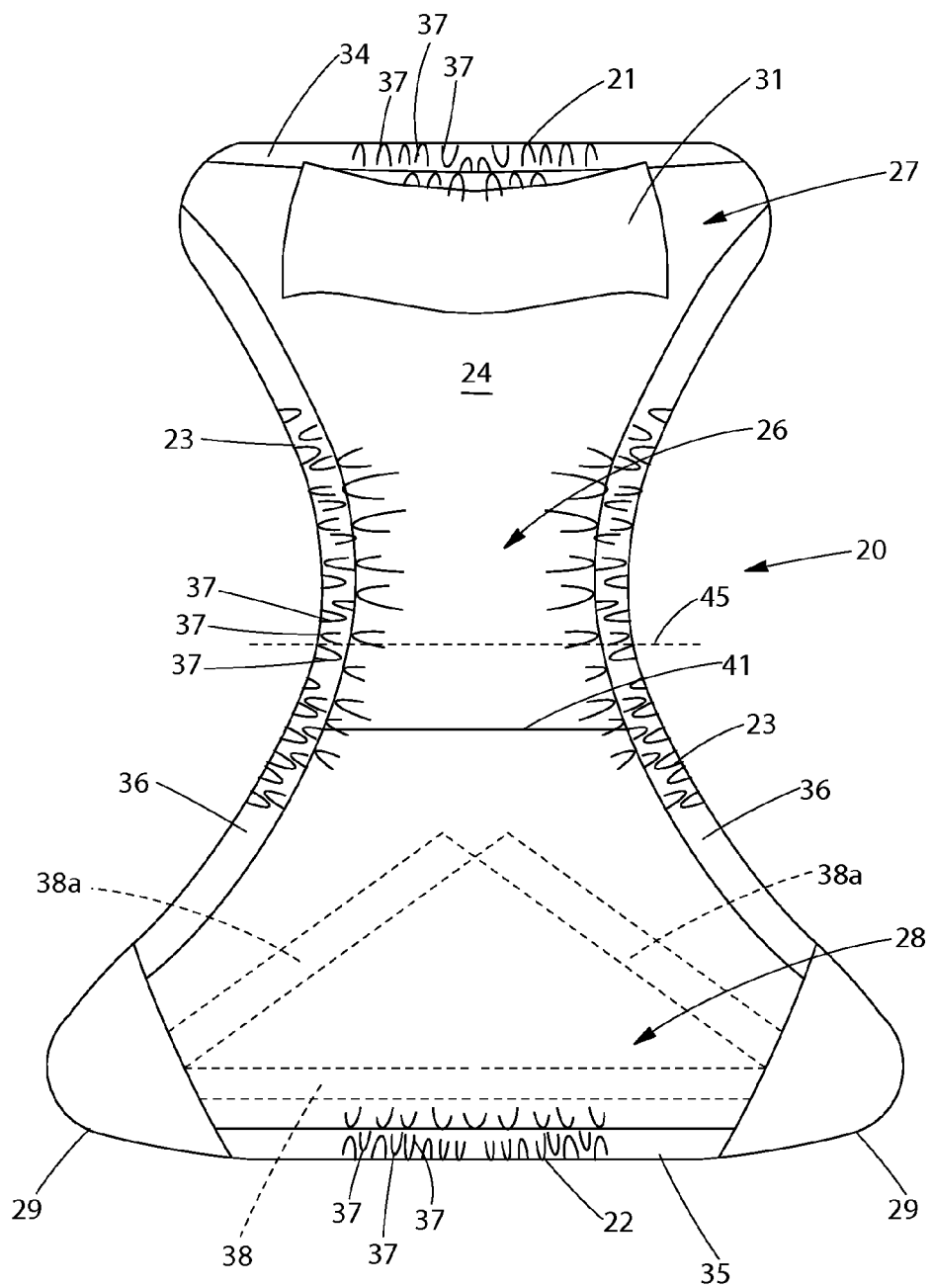
FIG. 2A is a plan view of an outer cover opened and laid flat, outer surface facing the viewer.
Figure 2B:
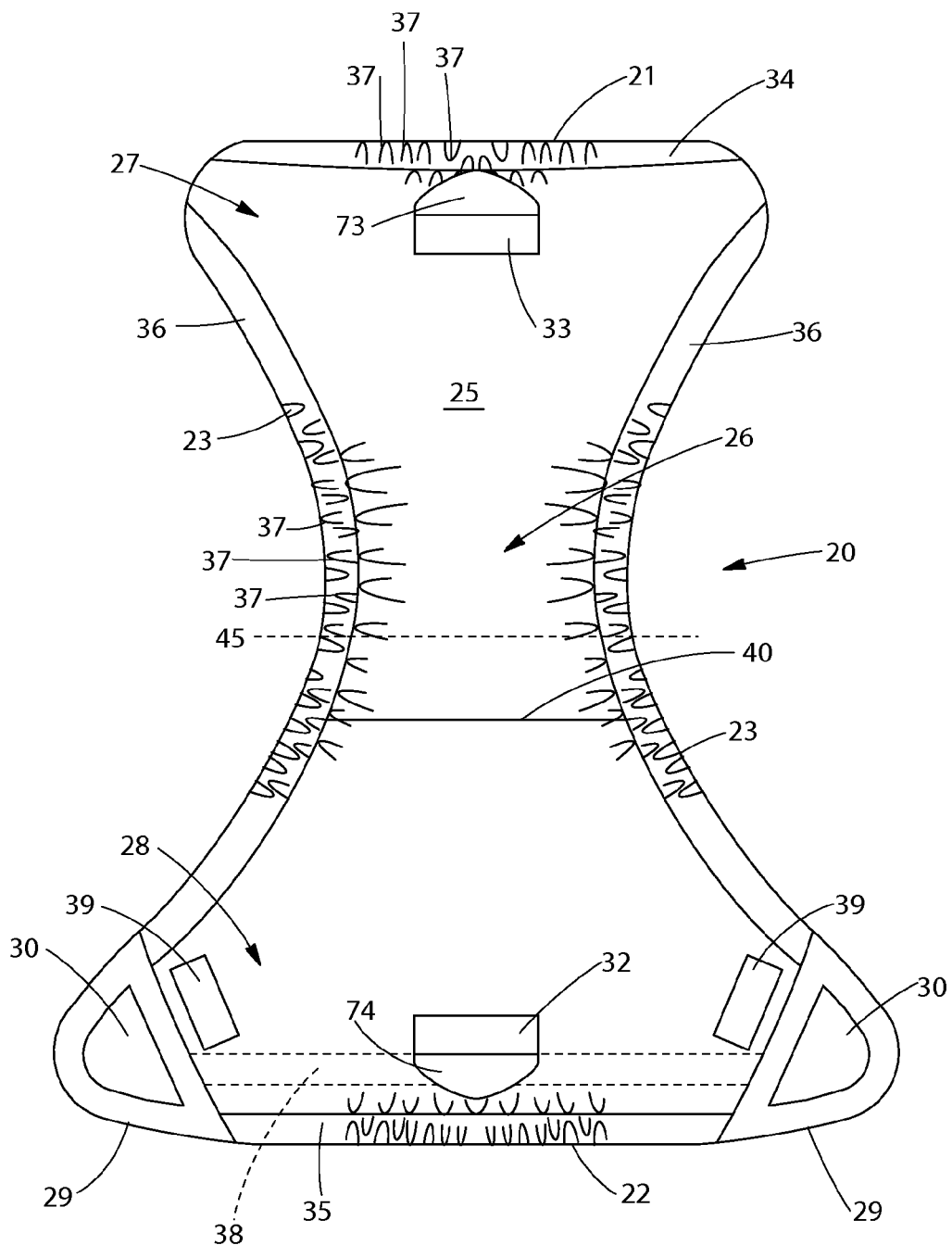
FIG. 2B is a plan view of an outer cover opened and laid flat, inner surface facing the viewer.
Figure 2C:
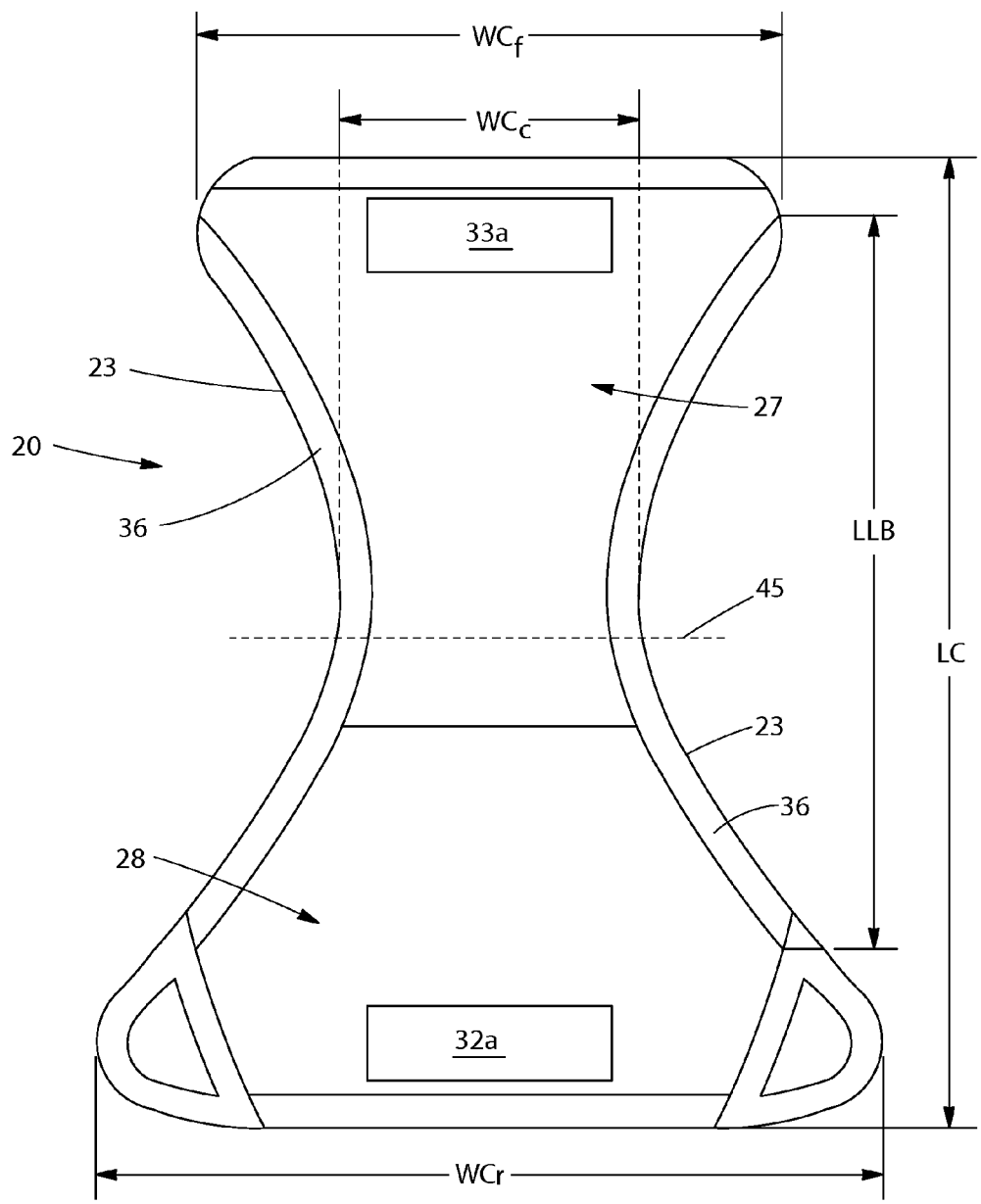
FIG. 2C is a plan view of an outer cover opened and laid flat, inner surface facing the viewer.

FIGS. 2A, 2B and 2C depict an outer cover 20 as it may appear opened and laid flat. In FIG. 2A, the outer, i.e., garment-facing, surfaces of outer cover 20 face the viewer; in FIGS. 2B and 2C, the inner, i.e., wearer-facing, surfaces of outer cover 20 face the viewer. Front and rear waist edges 21, 22 are depicted at the top and bottom of the drawings, respectively. Outer cover 20 may have crotch region 26, front region 27, rear region 28 and a pair of fastening ears 29 laterally extending from rear region 28. Outer cover 20 will have a length LC from the forwardmost portion of front waist edge 21 to the rearwardmost portion of rear waist edge 22, and an outer cover lateral axis 45 equally dividing this length. Thus, front region 27 is forward of outer cover lateral axis 45, and rear region 28 is rearward of outer cover lateral axis 45. Outer cover 20 may have disposed thereon one or more insert fastener components such as front and rear insert fastener components 33, 32.

Figure 3:
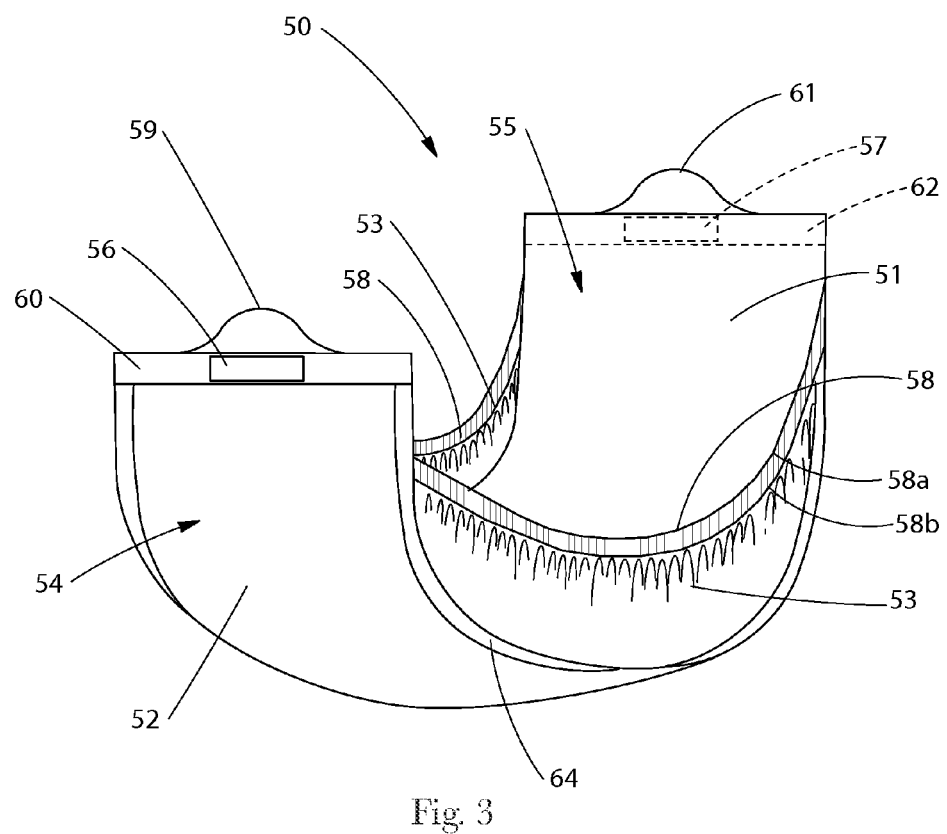
FIG. 3 is a perspective view of a disposable absorbent insert shown apart from an outer cover, as it might appear in a free-standing, relaxed state.
Figure 4:
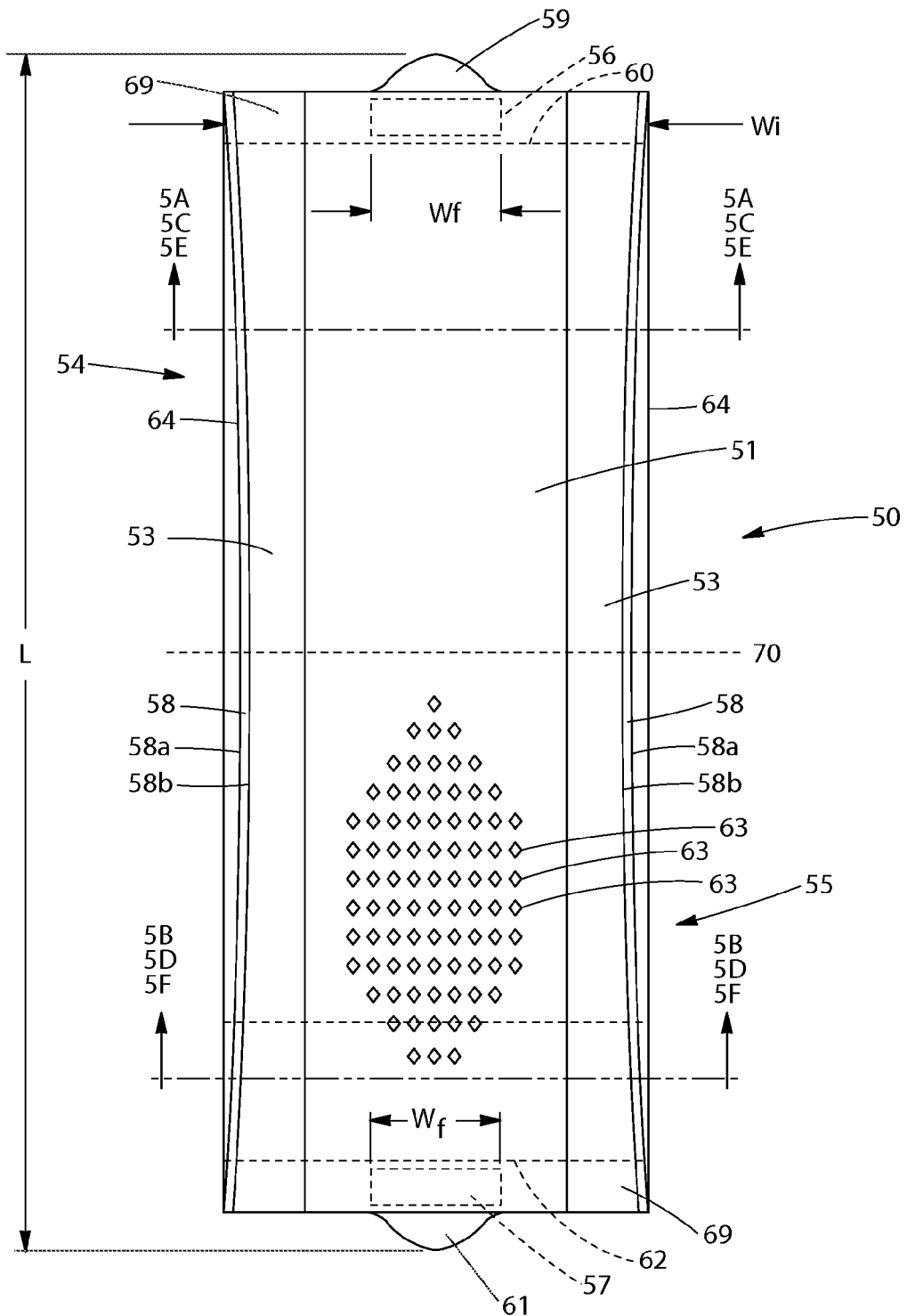
FIG. 4 is a plan view of a disposable absorbent insert shown stretched out and laid flat, body-facing surfaces facing the viewer.

FIG. 3 depicts a disposable absorbent insert 50 that may form an inner component of the wearable absorbent article 10, shown in perspective view as it might appear in a free-standing, relaxed state, apart from outer cover 20. Insert 50 may be designed to contain and/or absorb body exudates, and may be made of pliable materials as will be described further below. Insert 10 has forward region 54 and rearward region 55, and may include front fastener component 56 and rear fastener component 57. Insert 10 may include a body-facing liner or topsheet 51, outer liner or backsheet 52, and a pair of standing cuffs 53. Referring to FIG. 4, insert 50 will have a length L from the forwardmost portion of forward region 54 to the rearwardmost portion of rearward region 55, and an insert lateral axis 70 equally dividing this length. Thus, forward region 54 is forward of insert lateral axis 70, and rearward region 55 is rearward of insert lateral axis 70.

Referring to FIGS. 2B and 3, insert 50 may have rear fastener component 57 disposed thereon. Alternatively, or in addition, outer cover 20 may have rear insert fastener component 32 disposed thereon. Similarly, insert 50 may have front fastener component 56 disposed thereon. Alternatively, or in addition, outer cover 20 may have front insert fastener component 32 disposed thereon. If a two-component fastening system is used, fastener component pairs 57, 32 and 56, 33 may be cooperating components that effect fastening therebetween when these respective components are brought together. Thus, in the example depicted, in order to install absorbent insert 50 into outer cover 20, a user may lay outer cover 20 flat, inner surface 25 facing up, stretch and orient insert 50 such that rear fastener component 57 faces rear insert fastener component 32 and front fastener component 56 faces front insert fastener component 33, and bring these respective fastener component pairs 57, 32 and 56, 33 together to effect fastening therebetween.

If it is desired that outer cover 20 be reusable, for outer cover 20 to remain substantially sanitary and useful (without requiring laundering or disposal) after removal and replacement of an insert, it may be desired that all parts of outer cover 20 remain substantially unsoiled after an exudation of waste (especially fecal matter) by the wearer. Thus, it may be desired that when insert 50 is installed within an outer cover 20, there is no non-removable portion or component of outer cover 20 that lies over or covers a substantial portion of wearer-facing surfaces of insert 50 (expressed differently, no non-removable portion or component of outer cover 20 is situated between a substantial portion of insert 50 and the wearer when the wearable absorbent article is worn), at least in the areas proximate to wearer body features that discharge exudates. Thus, it may be desired that outer cover 20 include no non-removable cover sheet or the like that covers or contains substantial portions of wearer-facing surfaces of insert 50 within outer cover 20, nor any overlying structures such as pockets, straps or flaps that substantially wrap or cover the insert proximate to exudate discharge points, or lie substantially between insert 50 and the wearer's anus and/or genitals, when the wearable absorbent article is worn. If outer cover 20 lacks such overlying structures, this may increase the likelihood that the wearer's exudates will contact only insert 50, and not portions of outer cover 20.

Referring to FIGS. 1, 2A and 2B, it can be seen that wearable absorbent article 10 may be placed on a wearer by wrapping outer cover 20 between the wearer's legs and under the buttocks such that crotch region 26 is between the wearer's legs, bringing front waist edge 21 and rear waist edge 22 into the positions approximately as shown in FIG. 1, and then securing fastening ears 29 to front region 27, thereby forming a pant-like garment about the wearer as suggested in FIG. 1. When insert 50 has been installed into outer cover 20, insert 50 will then be disposed within outer cover 20, next to the wearer, with the standing cuffs 53 oriented and extending longitudinally adjacent the inner portions of leg edges 23 (i.e., longitudinally between the wearer's legs).

Examples of Possible Outer Cover Details

Fastening System

Referring to FIGS. 2A and 2B, to enable fastening of fastening ears 29 to front region 27, fastening ears 29 may have outer cover fastener components 30 disposed thereon. Alternatively, or in addition, front region 27 may have disposed thereon one or more receiving fastener components 31 disposed thereon. Fastener components 30, 31 may be selected so as to be cooperative to effect fastening of ears 29 to front region 27.

In one example, outer cover fastener components 30 may include a patch of hooks, and receiving fastener component 31 may include a patch of loops. An example of a suitable hook-and-loop fastening system is a VELCRO system (a product of Velcro Industries B.V.) A hook-and-loop fastening system provides certain advantages. Because the respective hook and loop components are supplied in sheet form, they may be cut into suitably shaped patches that can be affixed to a cloth or nonwoven substrate by various mechanisms, including adhesive bonding, mechanical bonding, ultrasonic bonding, sewing, stitching, serging, edging, and the like. If patches of hooks or loops are affixed to fastening ears 29 to form outer cover fastener components 30, as suggested by FIG. 2B, a laterally extended patch of cooperating hook or loop material can be affixed to outer cover front region 27 to form a receiving fastener component 31, as suggested by FIG. 2A. By providing for fastening of ears 29 to front region 27 at laterally varying locations thereon, this arrangement provides for easy and simple adjustability of waist opening size of the wearable absorbent article.

In another example, as noted above, the outer cover fastening system may include other types of fastener components. To provide for waist opening size adjustability, fastener components disposed on fastening ears 29 that cooperate with extended surfaces or multiple cooperating fastener components disposed on front region 27 may be used. Receiving fastener components may be multiply disposed on front region 27 in laterally arranged, varying locations, allowing for fastenability of respective ears 29 to front region 27 at laterally varying locations.

Referring to FIG. 2B, outer cover 20 also may have one or more respective fastener protectors 39 disposed thereon. This feature may prevent fastener components having features likely to randomly and unintentionally engage and catch on portions of the outer cover, or other articles, during storage, carrying, laundering and similar/related activities, from doing so, thereby avoiding potential bunching, entangling and/or damage to either outer cover 20 or other articles during such activities. For example, if fastener components 30 are patches of hooks, appropriately placed fastener protectors 39 may include patches of corresponding loops. This will enable the user to fold ears 29 over to engage them with fastener protectors 39, thereby holding them in the folded-over position such that hooks thereon will be concealed and prevented from snagging other articles when outer cover 20 is not being worn.

Materials

Outer cover 20 and/or layers or portions thereof may be made of any knitted, woven or nonwoven textile or textile-like material that is appropriately compatible with skin of the intended wearer(s). Outer cover 20 may be constructed of durable and/or semi-durable materials. Generally, only for purposes of reference in this description, "durable" refers to a woven or knitted textile material of any kind that may be used as a component of a washable clothing article. As used herein, "durable" includes materials which are "launderable" as defined and described in co-pending U.S. application Ser. Nos. 12/687,412; 12/687,528; and 12/687,425, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on the same day hereof. Generally, only for purposes of this description, "semi-durable" refers to a nonwoven material or laminate thereof that when used as an outer cover material can withstand more than one use with an insert without losing its structural integrity to an extent that renders it unserviceable. As used herein, "semi-durable" includes materials which are "laundering resistant" as defined and described in the co-pending U.S. applications identified immediately above. Thus, outer cover 20 may be constructed of materials and construction that make it reusable and/or washable.

Durable materials of which outer cover 20 may be constructed may include any natural or synthetic textile materials known in the diaper, pant, underwear, performance clothing, sport clothing, or general clothing or textile arts. Durable materials may include woven or knitted textiles made of natural fibers such as cotton, linen, wool, bamboo, hemp, silk, rayon, and the like, as well as blends of any of these fibers with any other(s), or with synthetic fibers. Examples of synthetic fibers suitable for use as components of durable materials include polyester, nylon, spandex and/or other elastomer fibers. Durable outer cover materials also may include breathable water repellent materials such as GORE-TEX (a product of W. L. Gore & Associates, Inc., Elkton, Md.), fabrics comprising microencapsulated phase-change polymer materials such as OUTLAST COMFORTEMP fabrics (products of Outlast Technologies, Boulder, Colo.—see U.S. Pat. No. 6,514,362 and U.S. Pat. No. 6,207,738, for example), COOLMAX (a product of Invista, Wichita, Kans.), and the like.

Suitable durable materials may be formed in any weave or knit fabric form, including birdseye fabric, terry, fleece, flannel, knits, stretch knits, sherpa, suedecloth, microfleece, satin, velour, Burley knits, etc. Suitable examples include POLARTECH POWER DRY, POWER STRETCH and WIND PRO (products of Polartec, LLC, Lawrence, Mass.). Knitted textiles, which may be more inherently stretchable and elastic than woven or nonwoven materials, may impart better fit, comfort and/or appearance to the outer cover. Incorporation of fibers of spandex or other elastomer also may also enhance stretchability and elasticity, and thereby impart better fit, comfort and/or appearance to the outer cover, than textiles not including such elastomeric fibers.

Specific suitable examples for durable outer cover materials include jersey knits of blends of: rayon (93%) and spandex (7%) fibers; modal (94%) and spandex (6%) fibers; cotton and spandex fibers; and bamboo and spandex fibers. Materials that have stretch capability of equal to or greater than about 2× may be desired. Suitable examples of materials may have basis weights of about 0.09-0.15 gram/in.$^2$ per layer, or other basis weights.

Durable outer cover materials may be selected to impart desired comfort, appearance and performance to outer cover 20. In some circumstances it may be desired to select durable outer cover materials which are sufficiently inexpensive to allow for disposal, if soiled extensively or damaged, with minimized issues of cost or conscience.

Semi-durable outer cover materials may include any natural or synthetic nonwoven web and/or film materials known in the diaper or pant arts. Semi-durable materials of which outer cover 20 may be constructed may include non-woven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of outer cover 20.

Non-limiting examples of fibers, nonwovens and laminates of nonwovens and films that might be considered for use as semi-durable outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Published Applications Nos. 2008/0319407; 2008/0045917; 2007/0293111; 2007/0287983; 2007/0287348; 2007/0249254; 2007/0203301; and 2005/0164587.

Semi-durable outer cover materials also may be selected to impart desired comfort, appearance and performance to outer cover 20. In some circumstances it also may be desired to select semi-durable outer cover materials which are sufficiently inexpensive to allow for disposal, if soiled extensively or damaged, with minimized issues of cost or conscience.

The outer cover also, or additionally, may include a laminated or substantially separate film layer, which may be elastic, to provide enhanced liquid penetration resistance and/or elastic properties. Elastic properties also can be added or enhanced via the addition of other materials to the outer, cover in layer, band or strip fashion, including elastic strands, bands, scrims, and the like. A film layer may be laminated with a durable material or semi-durable material. A film layer may include an elastomer based on KRATON (a product of Kraton Polymers U.S., LLC, Houston, Tex.), or by way of further example, VISTAMAXX available from ExxonMobil Chemical Company, Houston, Tex.; FLEXAIRE, EXTRAFLEX or FABRIFLEX (products of Tredegar Film Products Corporation, Richmond, Va.), and various latex-free elastomeric sheets available from Fulflex Elastomerics Worldwide (Greenville, Tenn.).

Inclusion of an elastomeric material, either as a fibrous component of a cloth or nonwoven layer, or as a film layer, provides for improved stretchability and elasticity where it may be deemed useful to accommodate the wearer's anatomy and movements, such as over the wearer's buttocks and/or around the waist areas, and improved fit and comfort. Additionally, where a film layer may be included, it may impart additional liquid containment capability to the outer cover. A film layer may include a film that is substantially liquid impermeable, but vapor permeable, so as to provide breathability and reduce humidity within the outer cover while it is being worn, reducing chances for over-hydration of the skin where liquid containment capability is desired. A breathable film also may be provided by mechanically perforating or aperturing a film by various processes. Examples of such processes are described in co-pending U.S. application Ser. Nos. 12/366,825 and 12/534,353.

Referring to FIG. 2A, in one example outer surface 24 may be formed by a first layer of a durable or semi-durable material. The material selected may include fibers having hydrophobic properties, providing enhanced liquid containment attributes to such first layer. In another example, however, it may be desirable in some circumstances for the selected material to include hydrophilic fibers, or fibers treated to be hydrophilic, so as will cause the material to more readily absorb and/or transmit liquid therethrough. This may serve to provide supplemental absorbency within the outer cover for the event in which liquid exudates escape the insert, or to provide one way of communicating to the user that liquid exudates have escaped the insert. Additionally, in some circumstances it may be desirable that the material selected have soft tactile properties so as to have a pleasant feel that the user and/or wearer find attractive. The material also may be selected so as to have a desired appearance, including but not limited to coloration, sheen, texture, etc.

Outer cover 20 may be formed of a single layer of a durable or semi-durable material, or may have two or more layers in the front region 27 and/or rear region 28. Accordingly, referring to FIG. 2B, in another example inner surfaces 25 may be formed by a second layer of a durable or semi-durable material. The material selected may include fibers having hydrophobic properties, providing enhanced liquid containment attributes to the second layer. In another example, however, it may be desirable in some circumstances for the selected material to include hydrophilic fibers, or fibers treated to be hydrophilic. This may be desired in some circumstances to cause the material forming inner surfaces 25 to more readily absorb liquid, or transmit liquid therethrough. This may serve to provide supplemental absorbency within the outer cover for an event in which liquid exudates escape the insert, reducing the likelihood that the outer cover will leak. Alternatively, it may provide one way of communicating to the user that liquid exudates have escaped the insert, by causing wetness to be transmitted through to the outer cover outer layer such that wetness is visible on outer surfaces. Alternatively, it may serve to provide a layer that tends to draw moisture away from the skin, for a drier, more comfortable feel.

Additionally, in some circumstances it may be desirable that the material(s) selected for inner surfaces 25 have soft tactile properties so as to have a pleasant feel against the skin, particularly in areas where no portion of an insert is expected to be present between the outer cover and the wearer's skin.

In another example, the second layer of material may be formed of a textile material having enhanced elasticity, such as by inclusion of fibers of an elastomeric material (such as spandex). In another example, an intermediate film layer may be included, laminated or not laminated with another layer.

Forming the outer cover 20 of more than one layer, for example, two, or more, layers, as described above, may provide various benefits. A second layer (and any additional layers) may provide supplemental tensile strength in both the lateral and longitudinal directions across the outer cover 20. Additionally, a first layer may be selected for a first set of properties, and a second layer may be selected for a second set of properties. For example, material forming a first layer may be selected for having comparatively greater elasticity and a particular texture, color and/or other appearance-related properties, and material forming a second layer may be selected for having comparatively greater hydrophobicity, hydrophilicity and/or softness to the skin for purposes of an inner layer, the two layers in combination imparting a combination of desirable attributes to the outer cover. For example, the inner layer may be formed of material(s) and/or treated to be more hydrophilic so as to provide for absorbency and reduced chances of fluid runoff (leakage), while the outer layer may be formed of material(s) that are more hydrophobic, so as to, e.g., resist environmental soiling, or resist liquid transmission from the inner layer to the outer layer. Additionally, a plurality of layers may better serve to conceal bumps, corners, seams or other features of an insert, as compared with a single layer, for a smoother, more attractive appearance.

In addition to forming differing layers of differing materials, it may be desirable to form a single layer of differing materials, for example, differing materials in the respective front, crotch and/or rear regions of the outer cover. Such differing materials may be joined at a seam such as inner seam 40 and/or outer seam 41. For example, the material predominately forming the inner surface of rear region 28 may be selected primarily for its elasticity features, which may better serve to provide snug fit about wearer body contours and accommodate wearer movement (i.e., about the buttocks and hips). By comparison, the material predominately forming the inner surface of front region 27 and/or crotch region 26 might be selected primarily for its hydrophobicity or hydrophilicity, which may better serve to contain liquid exudates.

Layers or other elements of the outer cover may be joined to each other via any suitable mechanism, including, for example, adhesives, mechanical bonding, ultrasonic bonding, sewing, stitching, serging, edging, and the like.

Additionally or alternatively to the constructions and materials described above, the outer cover may be constructed and may include materials and features as described in co-pending U.S. application Ser. Nos. 12/687,412; 12/687,528; and 12/687,425, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on the same day hereof.

Elasticized Waistbands, Leg Bands

Referring again to FIGS. 1, 2A and 2B, front waist band portion 34, rear waist band portion 35, and leg band portions 36 are depicted. One or more of these band portions 34, 35, 36 may be formed of one or more strands or strips including an elastomeric material such as spandex or a blend of spandex and other fibers, enveloped by a nonwoven or textile material, which may include the edges of the material forming the inner and/or outer layers of outer cover 20, to form and elasticize the respective band portions. The elastic material may be affixed to or within an outer cover layer in a strained condition, or at zero applied strain. Textile material(s) enveloping the elastic strand(s) or strip(s) may be sewn around elastic strand(s) or strip(s) to hold them in place within the respective band portions. If the elastic material is strained prior to, and while, being enveloped and affixed to form these band portions during the manufacturing process, upon relaxation the enveloping material and adjacent outer cover material may be caused to gather and form ruffles 37 therealong, which constitute gathered outer cover material. This can serve to promote snug fit, wearer comfort and appearance. The band portion may be disposed along the edge of the outer cover, and in some circumstances it may be desired to have the band portion situated along substantially the entire length of the leg and/or waist openings so as to form bands that substantially or completely encircle the wearer's legs and/or waist while outer cover 20 is worn. The gathered material within ruffles 37 can serve to accommodate stretching of waist band portions 34, 35 and leg band portions 36. This arrangement including elasticized leg band portions 36 as described, not only may provide for better fit about the wearer's legs, but also may enable the outer cover 20, when formed of appropriately sized and shaped material, to form a pouch-like structure 75 in the crotch region (see FIG. 1) when worn, which may serve to provide space within the outer cover to accommodate the insert 50 (FIG. 3) and help hold it in place within outer cover 20, in a substantially laterally centered position within the crotch region. This may be deemed advantageous in examples in which an insert 50 is attached within outer cover 20 by fastener components only located proximate to the respective ends of insert 50, and not at any longitudinally intermediate locations, as described further below. Alternatively, or additionally, the elastic strands or strips in waist band portions 34, 35 and leg band portions 36 may be affixed within the outer cover only at or near their respective ends, e.g., within a pouch, tube or envelope structure formed of outer cover material—referred to herein as a "drawstring elastic". This will allow the elastic material and associated outer cover material to stretch and move freely and independently of each other, which may promote fit and comfort. A snug fit about the wearer's legs provided by such elasticized leg band portions 36 may serve to enhance containment capability of the wearable absorbent article.

One or more of waist band portions 34, 35 and leg band portions 36 may be elasticized in the manner described above, or by other mechanisms. For example, elasticized band/strip material such as that used to form elastic waistbands and leg bands or other banding features of conventional cloth underwear, briefs or other articles of clothing may be separately produced, and affixed to the materials forming outer cover 20 in any suitable manner, during the manufacture thereof.

In another example, one or more of waist band portions 34, 35 and leg band portions 36 may be formed of elastic material simply affixed about the leg opening and/or waist opening edges by use of adhesive and/or compression bonding. In another example, an elastic strip material may formed by affixing a plurality of strained elastomeric strands or strips to one or more strips of unstrained nonwoven web material or film. When the resulting elastic strip material is allowed to relax, the unstrained material forms transverse rugosities that comprise gathered unstrained material, which will accommodate stretching of the elastic strip material. By affixing the elastic strip material at one or more of waist band portions 34, 35 and/or leg band portions 36, the elastic strip material may be used to form one or more of elasticized waist band portions 34, 35 and/or leg band portions 36.

Anchoring Bands

Outer cover 20 also may include an anchoring supplement such as anchoring band 38 disposed on or in the outer cover rear region 28 as indicated in FIGS. 2A, 2B. As suggested in FIGS. 2A and 2B, anchoring band 38 may be affixed along a layer, or disposed between layers, forming inner surfaces 25 and outer surfaces 24 of outer cover 20. Anchoring band 38 may include an elastomeric or elasticized strip or band of material, affixed to outer cover 20 at locations proximate to its rearward corners or proximate to fastening ears 29. Thus, anchoring band 38 may be partially or substantially force-decoupled from the other layer(s) of the outer cover along its lateral length from the layer(s) forming the inner and outer surfaces of outer cover 20, via attachment to the outer cover only by the ends of anchoring band 38, or only at a limited number of selected intermediate lateral locations along anchoring band 38. For example, anchoring band 38 might be attached to outer cover 20 only at the ends of anchoring band 38. In another example, anchoring band 38 might be attached to outer cover 20 only at the ends and at the lateral center of anchoring band 38. This substantially force-decoupled arrangement allows anchoring band 38 and surrounding portions of outer cover 20 to stretch and move substantially independently of one another, which may promote better fit and comfort. In another example, however, anchoring band 38 may be an elastic band, strip or strap laminated with or otherwise affixed to a layer of stretchable material forming either of or both the inner and outer surfaces of the outer cover, along substantially the entire length of anchoring band 38.

When strained laterally by application to the wearer, anchoring band 38 may serve to provide, or supplement, lateral tensile forces in the article about the wearer's waist, thereby tending to draw the waist opening snug, enhancing fit and enhancing securement of the wearable absorbent article about the wearer's waist. The elastic modulus of the anchoring band may be higher than the elastic modulus of the surrounding, adjacent, or coextensive outer cover materials.

An anchoring band, or system of one or more anchoring band members, may have any additional features described in, for example, co-pending U.S. patent application Ser. Nos. 11/810,741; 11/810,708; 12/101,476; 12/028,317; 11/810,745; 11/810,742; 11/810,734; 11/810,779; 11/810,715; 11/810,733; 11/810,736; 11/810,777; and 11/599,862; 11/810,901 and 11/599,851; 11/899,812; 12/204,844; 12/204,849; 12/204,854; 12/204,858; and 12/204,864; 11/899,810; 11/899,656; and 11/899,811; 11/899,812; 12/204,844; 12/204,849; 12/204,854; 12/204,858; and 12/204,864; and co-pending U.S. application Ser. Nos. 12/687,437; 12/687,554; and 12/687,444, entitled, respectively, "REUSABLE WEARABLE ABSORBENT ARTICLES WITH ANCHORING SYSTEMS," "REUSABLE WEARABLE ABSORBENT ARTICLES WITH ANCHORING SUBSYSTEMS," and "REUSABLE OUTER COVERS FOR WEARABLE ABSORBENT ARTICLES," by Donald C. Roe, filed on the same day hereof.

In another example, instead of, or in addition to, being oriented substantially laterally as suggested by the depicted location of anchoring band 38 in FIGS. 2A and 2B, one or more members forming anchoring bands may be oriented diagonally between the longitudinal and lateral directions. For example, as suggested in FIG. 2A, a pair of diagonal anchoring bands 38a may have respective waist ends thereof affixed at a location area proximate to corners of the outer cover and/or fastening ears 29, and respectively extend toward both the lateral and longitudinal center of outer cover 20, as suggested in FIG. 2A. The respective center ends of bands 38a may be affixed to the outer cover at locations proximate the lateral center of the outer cover as suggested in FIG. 2A, and bands 38a may be either force-decoupled or force-coupled to the outer cover along the lengths of bands 38a, as described above. In an example where an insert is connected to an anchoring band for additional longitudinal support as described further below, diagonal anchoring bands such as diagonal anchoring bands 38a may serve to provide supplementary longitudinal tension along outer cover 20, providing supplemental longitudinal support therewithin.

Outer Cover Asymmetry

In order to enhance and/or maximize fit, wearer comfort and appearance of the outer cover 20, it may be desirable to fashion outer cover 20 so as to accommodate anatomical contours and body movements of the intended wearer. For example, as suggested by FIGS. 2A and 2B, outer cover 20 may have differing shape and/or greater material surface area in the rear region 28 than in the front region 27. Human anatomy in the lower torso/hip/thigh region is asymmetric about the lateral plane of the body, i.e., the geometry of the front of the human body is different than that of the back. To provide for better fit and comfort, the outer cover geometry and functionality, including stretch properties, may be adapted accordingly. Differing shape and/or greater material surface area in the rear region may serve to better cover the buttocks through movements of the wearer (including sitting and/or bending forward at the hips), while lesser material surface area in the front region may serve to avoid material bunching and/or an ill-fitting appearance, particularly when the wearer is in positions including sitting and/or bending forward at the hips. As a result, the outer cover may be asymmetric in shape or surface area across outer cover lateral axis 45.

For purposes of this description, when used with respect to an outer cover, "asymmetric" and "asymmetry" mean that features, geometry (e.g., shape), materials and/or construction on one side of outer cover lateral axis 45 differ substantially in some respect from those on the other side of outer cover lateral axis 45. Such asymmetric construction results from having various features of outer cover 20 designed to accommodate the body features and functions of the intended wearer as they differ front-to-rear, to enhance containment/absorbency performance, comfort, fit and/or appearance of the wearable absorbent article, and/or to economize on use of materials. "Asymmetric" and "asymmetry" do not refer to differences across the outer cover lateral axis that are attributable to features that may be included on an outer cover only for purposes of: purely cosmetic coloration or surface decoration; fastening an insert (such as fastener components described herein); bundling, folding, storing or carrying the outer cover; indicia for orienting an insert within an outer cover or vice versa (such as orientation indicia described herein), or for other purposes substantially unrelated to the body features and functions of the intended wearer as they differ front-to-rear, to affect performance, comfort, fit and/or physical appearance of the wearable absorbent article, and/or to economize on use of materials.

Other asymmetries across outer cover lateral axis 45 may be present as well. For example, as suggested by FIGS. 2A and 2B, relatively localized outer cover fastener components 30 may be respectively disposed on fastening ears 29, while a relatively laterally extended receiving fastener component 31 may be disposed on outer cover front region 27, for purposes of waist opening adjustability as explained above. Fastening ears 29 may form lateral extensions from rear region 28 that are not present in kind on front region 27. These are examples of differences that create functional and structural asymmetries of the outer cover across outer cover lateral axis 45. Because an absorbent article of the type described herein is usually changed while the wearer is substantially facing the user, such arrangement enhances user convenience by locating these fastening and waist opening adjustability features at the wearer's front abdominal region, facing the user.

In another example of asymmetry, materials of differing composition, construction and/or properties may predominately form forward region 27 as compared with rearward region 28. For example, the material(s) forming rear region 28 may be selected for enhanced stretch/elastic properties, as compared with material(s) forming front region 27. In this example, material(s) with enhanced stretch/elastic properties may serve to better accommodate, stretch and contract over contours of the buttocks, and accommodate body movements such as sitting and bending forward at the hips, thereby providing better coverage and fit.

In still another example of asymmetry, outer cover 20 may have structures such as elastic bands, anchoring bands and/or other members which differ between front region 27 and rear region 28.

In still other examples of asymmetry, the materials thinning outer cover 20 may have, or be imparted with, differing levels of hydrophilicity and/or hydrophobicity, differing levels of breathability, differing coefficients of friction, and/or other differing functional attributes in the front versus the rear regions.

It will be appreciated, therefore, that outer cover asymmetry across outer cover lateral axis 45 is a result of design and construction of the outer cover so as to have only one front region and only one rear region, i.e., the front and rear regions are not interchangeable, if the fit, comfort, performance and appearance of outer cover 20 are to be optimal.

Examples of Possible Absorbent Insert Details

Examples of features of an absorbent insert 50 will be described with reference to FIGS. 3, 4 and 5A-F.

As noted above, FIG. 3 depicts a disposable absorbent insert 50 that may form an inner component of a wearable absorbent article as described herein, shown in perspective view as it might appear in a free-standing, relaxed state, apart from an outer cover. FIG. 4 depicts an example of an insert 50 shown stretched out and laid flat (against elastic-induced contraction to a position similar to that shown in FIG. 3), body-facing surfaces facing the viewer. FIGS. 5A-5F depict cross sections of an insert 50 as indicated in FIG. 4, in various possible examples.

Insert 50 may have a topsheet 51 and backsheet 52 forming an envelope-like enclosure for absorbent core materials such as those described further below. Topsheet 51 and backsheet 52 may be affixed together along longitudinal seams 64, and along lateral seams 69. Insert 50 also may have longitudinal standing cuffs 53 affixed therealong.

Topsheet

Topsheet 51 may be formed of a liquid-permeable non-woven web material. It may be desired that material forming topsheet 51 is compliant, soft-feeling, and non-irritating to the wearer's skin. It may be desired that at least a portion of topsheet 51 may be liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If topsheet 51 includes fibers, the fibers may be spunbond, carded, wet-laid, meltblown, hydroentangled, or otherwise processed as is known in the art.

One suitable material comprising a nonwoven web of staple-length polypropylene fibers is manufactured by Veratec, Inc., a Division of International Paper Company, of Walpole, Mass. under the designation P-8. Additional suitable materials comprising formed films are described in U.S. Pat. Nos. 3,929,135; 4,324,246; 4,342,314; 4,463,045; and 5,006,394. Other suitable topsheets 30 may be made in accordance with U.S. Pat. Nos. 4,609,518 and 4,629,643. Suitable examples of formed and/or apertured films may include products produced by The Procter & Gamble Company of Cincinnati, Ohio as DRI-WEAVE, and by Tredegar Corporation, based in Richmond, Va., as FRESHFEEL. Suitable topsheet materials also may include laminates of films and nonwoven webs produced by Tredegar as COMFORTFEEL, COMFORTQUILT, SOFTQUILT and COMFORTAIRE.

In some circumstances it may be desired that at least a portion of topsheet 51 is made of a hydrophobic material or is treated to be hydrophobic in order to isolate the wearers skin from liquids contained in absorbent core 71. If topsheet 51 is generally made of a hydrophobic material, it may be desired that at least a portion of the upper surface of topsheet 51 is treated to be hydrophilic so that liquids will transfer through the topsheet more rapidly. Topsheet 51 can be rendered hydrophilic by treating it with a surfactant or by incorporating surfactant into the topsheet. Suitable methods for treating topsheet 51 with a surfactant include spraying the topsheet material with the surfactant and/or immersing the material into the surfactant. A more detailed discussion of such a treatment and hydrophilicity is contained in U.S. Pat. Nos. 4,988,344 and 4,988,345. A more detailed discussion of some suitable methods for incorporating a surfactant in the topsheet can be found in U.S. Statutory Invention Registration No. H1670. In another example, however, topsheet 51 may include an apertured web or film which is hydrophobic. This may be accomplished by foregoing the hydrophilizing treatment step from the production process and/or applying a hydrophobic treatment to the topsheet material, such as a polytetraflouroethylene compound like SCOTCHGUARD or a hydrophobic lotion composition, as described below. In such examples, it may be desired that the apertures be large enough to allow the penetration of aqueous fluids like urine without significant resistance otherwise attributable to hydrophobicity. It may also be desired that the apertures have sufficient effective open area and/or aperture size to allow the penetration of low-viscosity fecal material. Examples of topsheets meeting these requirements are described in U.S. Pat. Nos. 5,342,338; 6,414,215; and 6,010,491.

Any portion of topsheet 51 may be coated with a lotion or skin care composition as is known in the art. Examples of suitable lotions include those described in U.S. Pat. Nos. 5,607,760; 5,609,587; 5,635,191; 5,643,588; 5,968,025 and 6,716,441. The lotion may function alone or in combination with another agent as the hydrophobizing treatment described above.

Topsheet 51 may also include or be treated with antibacterial agents, some examples of which are disclosed in U.S. application Ser. No. 08/212,441, published as U.S. Statutory Invention Registration H1732.

Topsheet 51, backsheet 52 or any portion of the topsheet or backsheet may be embossed and/or matte finished to provide a more cloth-like appearance.

Topsheet 51 may be fully or partially elasticized or may be foreshortened so as to provide a void space between topsheet 51 and core 71. Exemplary structures including elasticized or foreshortened topsheets are described in more detail in U.S. Pat. Nos. 4,892,536; 4,990,147; 5,037,416; and 5,269,775.

Backsheet

Backsheet 52 is generally that outer liner portion of insert 50 forming the garment-facing surface thereof, and prevents the exudates absorbed and contained within insert 50 from wicking through and soiling the outer cover. In some circumstances it may be desired that backsheet 52 is substantially impervious to liquids.

Backsheet 52 may be formed of a film, a nonwoven, or a laminate of a film and a nonwoven. Backsheet 52 may be formed of a substantially liquid-impermeable laminate or composite of film and non-woven web. Backsheet 52 may be formed of a substantially liquid impermeable nonwoven web, or laminate of nonwoven web and substantially liquid impermeable film, so as to contain and isolate liquid exudates from the outer cover, outer clothing and/or environment of the wearer. At the same time, backsheet 52 may be vapor permeable to provide for breathability of the insert and the wearable absorbent article, reducing humidity in the areas between the insert and the wearer's body, and helping reduce the likelihood of skin irritation and/or rashes that may result from over-hydration of the skin.

The material forming backsheet 52 may include a thin plastic film such as a thermoplastic film having a thickness of about 0.012 mm (0.5 mil) to about 0.051 mm (2.0 mils). Suitable backsheet materials also may be breathable materials which permit vapors to escape while still preventing liquid from passing therethrough. Suitable examples may include those manufactured by Tredegar Corporation, based in Richmond, Va., and sold under the trade names CPC2, X15306, X10962 and X10964 film. Other examples may include microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some additional examples may include breathable composite materials as described in PCT Application No. WO 95/16746; and U.S. Pat. Nos. 5,938,648; 5,865,823; and 5,571,096. In other examples, backsheet 52 may comprise elastomeric films, foams, strands, or combinations of these or other suitable materials with nonwovens or synthetic films.

In certain embodiments, the backsheet may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity. A higher WVTR may be desired in this particular application, since the insert backsheet 52 will not form the outer surface of the wearable article, as a conventional disposable diaper backsheet would, but rather, will be covered by the one or more layers of the outer cover material(s)—which themselves may act in some circumstances to reduce WVTR of the composite structure.

Backsheet 52 may be joined to topsheet 51, absorbent core 71 or any other element of insert 50 by any suitable attachment mechanism known in the art. For example, the attachment mechanism may include a continuous line or layer of adhesive, a patterned layer of adhesive, or an array of separate lines, spirals, or spots of adhesive. One example of an attachment mechanism comprises an open pattern network of filaments of adhesive as disclosed in U.S. Pat. No. 4,573,986. Other suitable attachment mechanisms include several lines of adhesive filaments which are swirled into a spiral pattern, as is illustrated by the apparatus and methods shown in U.S. Pat. Nos. 3,911,173; 4,785,996; and 4,842,666. Adhesives which have been found to be satisfactory are manufactured by H. B. Fuller Company of St. Paul, Minn. and marketed as HL-1620 and HL-1358-XZP. Alternatively, the attachment mechanism may comprise heat bonds, pressure bonds, ultrasonic bonds, dynamic mechanical bonds, or any other suitable attachment mechanisms or combinations of these attachment mechanisms known in the art.

It will be appreciated that the outer cover described above can be constructed of materials and construction so as to bear and sustain a majority of the structural loading generally imposed upon a disposable diaper, by stretching and accommodation of the wearer's anatomical features and body movements, and by absorption, swelling and added weight resulting from the wearer's exudations of waste. Thus, lesser requirements for structural strength of an insert might be present with use of such an outer cover, as compared with strength required of inside components of a disposable diaper. Therefore, an article such as described herein may include a disposable absorbent insert manufactured from materials that are different from those ordinarily used in the manufacture of disposable diapers, such as petroleum-derived materials, e.g., polyethylene and polypropylene. For example, a disposable absorbent insert having one or more of a topsheet, backsheet, standing cuffs and/or other components formed of products of wood, cotton, flax (linen), hemp, bamboo, or other cellulose fibers (e.g., paper), in addition to the materials identified above, is contemplated. If resistance to aqueous liquid penetration or substantial liquid impermeability is desired, e.g., for a backsheet and/or standing cuffs, a material formed of ordinarily hydrophilic fibers such as paper may be coated or impregnated with a hydrophobic material, such as a skin-compatible oil or wax, to impart the desired resistance to aqueous liquid penetration. Each of the materials forming the insert may be selected so as to be dispersible in water or an aqueous solution, flushable, biodegradable and/or compostable (preferably to an agriculturally usable humus or soil amendment).

Absorbent Core

Referring to FIGS. 5A-F, insert 50 may have an absorbent core 71 within the envelope-like structure formed by topsheet 51 and backsheet 52. Absorbent core 71 may comprise any absorbent material which is generally compressible, conformable, non-irritating to the wearer's skin, and capable of absorbing and retaining liquids such as urine and other certain body exudates. Absorbent core 71 may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Absorbent core 71 may include liquid acquisition/distribution material 65, and storage material 66. Generally, acquisition/distribution material 65 may have comparatively rapid absorption and wicking properties, but also may have limited absorption capacity. Conversely, generally, storage material 66 may have comparatively slower absorption and wicking properties, but also may have greater absorption capacity. Thus, acquisition/distribution material 65 may serve to rapidly absorb and distribute gushes of liquid such as urine, while storage material 66, having greater absorption capacity, may serve to absorb such liquid from the acquisition/distribution material and store it for the time needed until the insert may be replaced.

Absorbent core 71 may be manufactured in a wide variety of sizes and shapes (e.g., rectangular, hourglass, "T"-shaped, etc.). The configuration and construction of absorbent core 71 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Examples of absorbent structures for use as absorbent core 71 may include those described in U.S. Pat. Nos. 4,610,678; 4,673,402; 4,834,735; 4,888,231; 5,137,537; 5,147,345; 5,342,338; 5,260,345; 5,387,207; and 5,625,222.

To reduce the overall size and/or thickness of the absorbent core, and thereby improve wearer comfort and reduce the volume of disposable waste created by a soiled insert, it may be desired to construct an absorbent core using the lowest volumes of core materials possible within performance constraints. Toward this end, examples of suitable materials and constructions for a suitable absorbent core are described in, but are not limited to, copending U.S. application Ser. Nos. 12/141,122; 12/141,124; 12/141,126; 12/141,128; 12/141,130; 12/141,132; 12/141,134; 12/141,141; 12/141,143; and 12/141,146. These applications generally describe absorbent core constructions that minimize or eliminate the need for and inclusion of airfelt or other forms of cellulose fiber in combination with particles of superabsorbent polymer (hereinafter, "substantially airfelt-free cores"). Airfelt and other cellulose fiber have been used as absorbent fillers in absorbent cores of disposable diapers. Such fiber possesses absorbent properties and imparts some absorption capacity to an absorbent core, but also is included to provide a structural matrix to hold dispersed particles of superabsorbent polymer and/or absorbent gelling material. While inclusion of such particles enhances absorption capacity, keeping such particles suitably dispersed may be important to prevent the particles from "gel-blocking" in use as they swell with absorbed liquid, causing loss of absorption capacity. The inclusion of airfelt or other cellulose fiber as a matrix for superabsorbent particles can serve to reduce or prevent gel-blocking. However, it also imparts bulk to an absorbent core, even before absorption of any liquids.

Figure 5A:
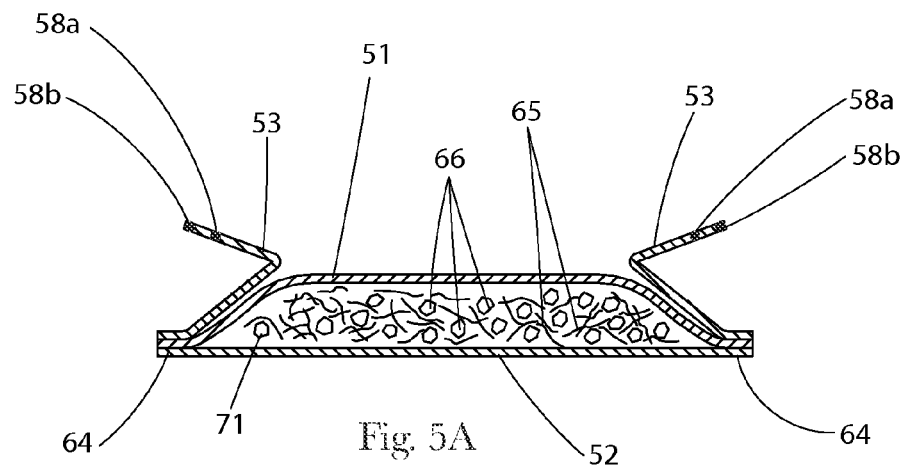
FIG. 5A is a cross sectional view of an example of an insert such as shown in FIG. 4, taken at line 5A-5A in FIG. 4.
Figure 5B:
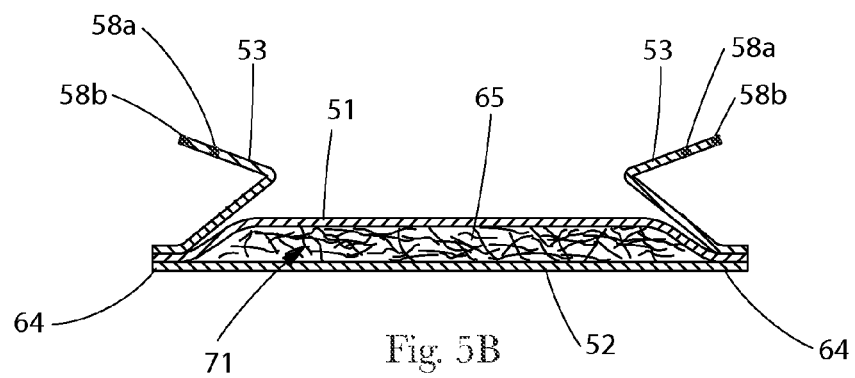
FIG. 5B is a cross sectional view of an example of an insert such as shown in FIG. 4, taken along line 5B-5B in FIG. 4.
Figure 5C:
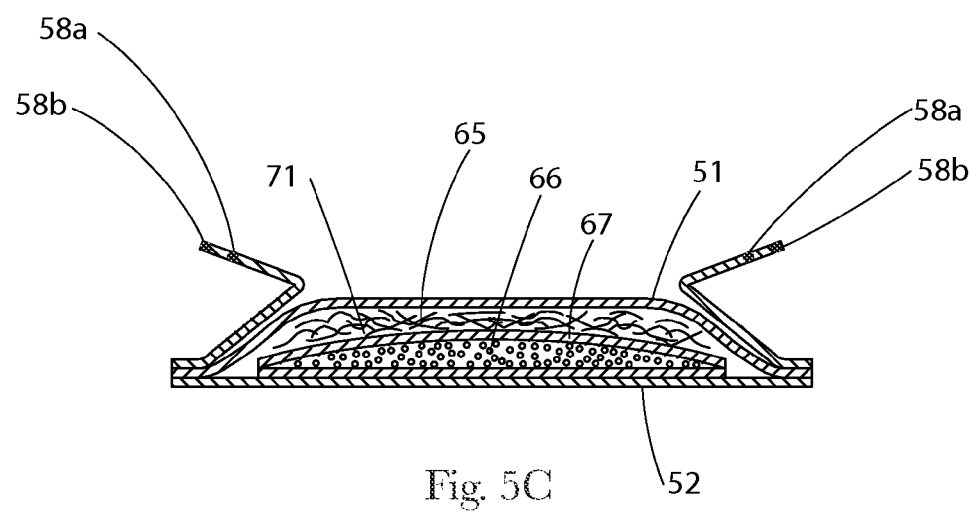
FIG. 5C is a cross sectional view of another example of an insert such as shown in FIG. 4, taken along line 5C-5C in FIG. 4.
Figure 5D:
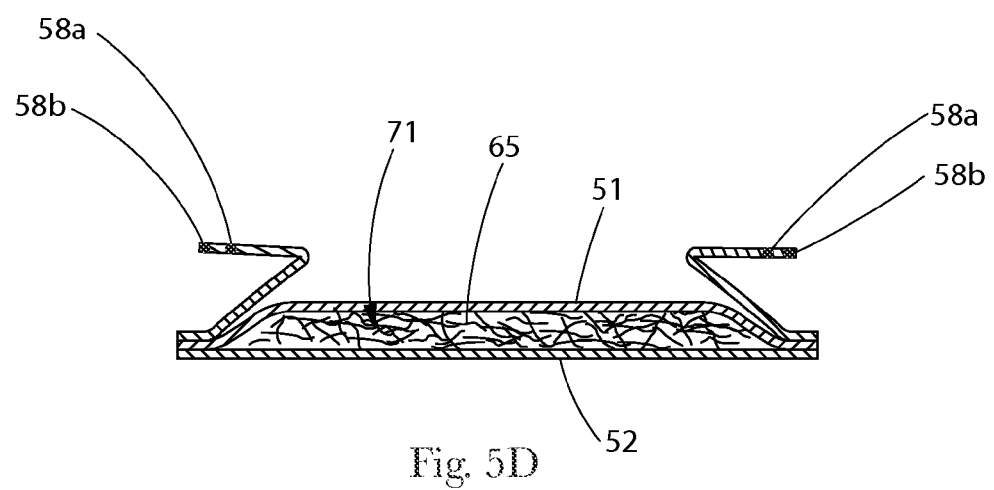
FIG. 5D is a cross sectional view of another example of an insert such as shown in FIG. 4, taken along line 5D-5D in FIG. 4.
Figure 5E:
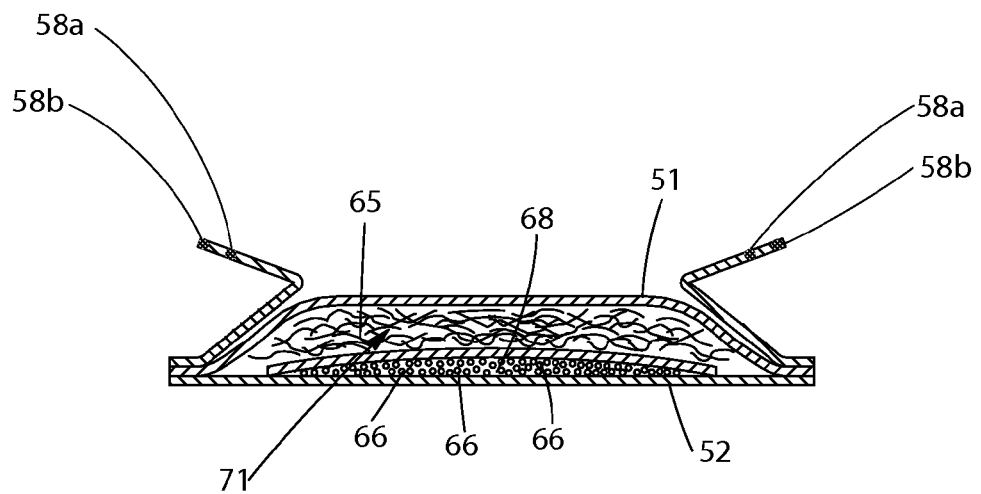
FIG. 5E is a cross sectional view of another example of an insert such as shown in FIG. 4, taken along line 5E-5E in FIG. 4.

In accordance with the disclosures in the co-pending applications identified immediately above, referring to the examples depicted in FIGS. 5C and 5E herein, an absorbent core 71 having a portion that is substantially airfelt-free may be disposed between the topsheet 51 and the backsheet 52. The core 71 may include a layer formed at least in part of a substrate, distributed absorbent particles 66 of a superabsorbent polymer or absorbent gelling material, and a thermoplastic adhesive composition capturing the distributed absorbent particles 66 and adhering to at least portions of the substrate, thereby immobilizing the absorbent particles 66 on or proximate to, and relative to, the substrate.

Features of an outer cover 20 as described herein provide for a wearable absorbent article that has a relatively improved, garment-like (or underwear-like) fit, comfort and appearance (as an outer garment or under other clothes), as compared with many types of wholly disposable diapers currently available. If an outer cover 20 having such attributes is used with an insert 50 having an absorbent core 71 incorporating substantial amounts of airfelt or other cellulose fiber, the improved, garment-like fit, comfort and appearance provided by the outer cover 20 may be compromised by the bulkiness of the insert. In order to better preserve some or most of the improved, garment-like fit, comfort and appearance of the outer cover 20, therefore, it may be desirable to construct absorbent core 71 of insert 50 with features as described in one or more of patent applications cited immediately above, which provide for a relatively thin absorbent core.

In addition to providing an absorbent core having reduced bulk, the substantially airfelt-free core may generally be more flexible than an absorbent core containing substantial amounts of airfelt or other cellulose fiber. This enhanced flexibility may enable the core and the associated insert to better conform about the wearer's body when in use, providing for improved comfort and less bulky appearance of the wearable article 10.

Additionally, by reducing or eliminating airfelt or other cellulosic fiber material, the substantially airfelt-free core reduces the amount of materials consumed in manufacturing, reduces the amount of space (and in some circumstances, weight) per unit which must be packaged and shipped, conserving resources in that regard, and reduces the amount of materials and bulk which must be disposed of in connection with disposing of a used/soiled insert.

Sublayer

Insert 50 may also include a sublayer disposed between topsheet 51 and backsheet 52. The sublayer may be any material or structure capable of accepting, storing or immobilizing bodily exudates. Thus, the sublayer may include a single material or a number of materials operatively associated with each other. Further, the sublayer may be integral with another element of insert 50 or may be one or more separate elements joined directly or indirectly with one or more elements of insert 50. Further, the sublayer may include a structure that is separate from the core 71 or may include or be part of at least a portion of the core 71.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One example of a sublayer includes a mechanical fastening loop landing element, having an uncompressed thickness of about 1.5 millimeters available as XPL-7124 from the 3M Corporation of Minneapolis, Minn. Another example includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Standing Cuffs

Insert 50 also may have a pair of longitudinal standing cuffs 53 attached partially or entirely along the length thereof. Suitable longitudinal standing cuffs (in various published examples identified as "leg cuffs", "barrier cuffs" "gasketing cuffs," etc., may be formed of materials and construction such as described in, but not limited to, U.S. Pat. Nos. 6,786,895; 6,420,627; 5,911,713; 5,906,603; 5,769,838; 5,624,425; 5,021,051 and 4,597,760; and copending U.S. Published Application No. 2007/0239130 and U.S. application Ser. No. 11/195,272. As shown in FIG. 3, standing cuffs 53 may have one or more strands or strips of cuff elastics 58a, 58b disposed longitudinally therealong. If such cuff elastics 58a, 58b are pre-strained prior to being affixed to the web material forming standing cuffs 53, resulting longitudinal tensile forces therealong will cause the web material forming standing cuffs 53 to gather as shown, and cause the cuffs to extend from the body of the insert (upwardly relative to FIG. 3), or causing them to "stand". This feature causes standing cuffs 53 to form a gasketing structure along the wearer's body when the article including insert 50 is worn, longitudinally on either side of the anatomical features where waste is exuded. Thus, standing cuffs 53 may serve to enhance the exudate containment capability of insert 50 and, and as a result, of the wearable absorbent article. As with backsheet 52, standing cuffs 53 may be formed of a substantially liquid impermeable web so as to contain and isolate liquid exudates from the outer cover, outer clothing and environment of the wearer. At the same time, standing cuffs 53 may be vapor permeable to provide for breathability of the insert and the wearable absorbent article, reducing humidity in the areas between the insert and the wearer's body, and helping reduce the likelihood of skin irritation and/or rashes that may result from over-hydration of the skin.

In another example, the material forming standing cuffs 53 may be integral with the material forming backsheet 52, such as described in, by way of non-limiting example, copending U.S. Published App. No. 2007/0239130. In this particular example, referring to and relative to the view in FIG. 3, a continuous piece of material may form one standing cuff 53, wrap beneath the insert to form backsheet 52, and wrap up the other side to form the other standing cuff 53. This example of a wraparound construction may provide improved liquid containment capability to insert 50, by eliminating seams along the outer liquid-containing surfaces that include standing cuffs 53 and backsheet 52. Another example of this construction is depicted and described in U.S. Pat. No. 4,808,178.

In some circumstances, however, manufacturing and/or economic constraints may discourage such construction, or else, it may be desirable for the materials forming standing cuffs 53 and backsheet 52 to have differing properties. For example, in some applications it may not be deemed necessary for standing cuffs 53 to be substantially liquid impervious, if they are otherwise formed of a nonwoven web material comprising closely situated hydrophobic fibers, which may still tend to repel and contain fluid, but may be generally more breathable than substantially liquid impervious laminates including films. In this event, improved strength and liquid containment attributes can still be imparted by having the material forming standing cuffs 53 wrap only partially beneath the lower longitudinal corners of the insert, and affixed at seams beneath the insert, rather than at its outermost lower corners as suggested by FIG. 3. One example of this construction is depicted and described in U.S. application Ser. No. 11/158,563, and in particular, FIG. 13 therein and associated descriptive text.

Insert Asymmetry

Referring to FIG. 4, insert 50 will have an insert lateral axis 70 that equally divides its longitudinal length. Insert 50 may have a structure that is asymmetric across insert lateral axis 70. For purposes of this description, with used with respect to an insert, "asymmetric" and "asymmetry" mean that features, geometry (e.g., shape), materials and/or construction on one side of insert lateral axis 70 differ substantially in some respect from those on the other side of insert lateral axis 70. Such asymmetric construction results from having various features of insert 50 designed to accommodate the body features and functions of the intended wearer (i.e., body contours, excretory and eliminatory functions) as they differ front-to-rear, to enhance containment/absorbency performance, comfort, fit and/or appearance of the wearable absorbent article, to economize on use of materials and/or to reduce volume of disposable waste. "Asymmetric" and "asymmetry" do not refer to differences across the insert lateral axis that are attributable to features that may be included on an insert only for purposes of: purely cosmetic coloration or surface decoration; fastening to an outer cover (such as fastener components described herein); user grasping of the insert (such as a grasping structure described herein); as indicia for orienting an insert within an outer cover (such as orientation indicia described herein); or for other purposes substantially unrelated to the body features and functions of the intended wearer as they differ front-to-rear, to affect performance, comfort, fit and/or physical appearance of the wearable absorbent article, to economize on use of materials and/or to reduce volume of disposable waste.

As one example, topsheet 51 may one or more have apertures 63 therethrough, predominately in the crotch and/or rearward region 55 as suggested in FIG. 4. Apertures 63 can permit liquid or low viscosity fecal material to penetrate topsheet 51 and reach absorbent materials in absorbent core 71 more rapidly than would occur without such apertures, enhancing liquid feces absorption and containment capability of insert 50.

In another example, a feces management feature may be disposed in the rear of the article, including one or more pockets, spacers, low viscosity feces management elements, openings in suspended elasticized topsheets, and similar features, for example, as described in copending U.S. application Ser. No. 11/224,779, 11/786,890 and 11/894,087. Thus, topsheet 51 may comprise one or more larger apertures in the rear region to provide for unrestricted or comparatively less restricted movement of solid or higher viscosity waste therethrough. The size of an aperture may be important in achieving the desired fecal waste encapsulation performance. If the aperture is too small, the waste may not pass through the aperture, either due to poor alignment of the exudation point and the aperture location, or due to fecal masses having a size greater than the aperture. If the aperture is too large, however, the area of skin that may be exposed to "rewet" from the contained waste matter is increased. An aperture may have an area of between about 10 cm$^2$ and about 50 cm$^2$. In some circumstances it may be desired that an aperture has an area of between about 15 cm$^2$ and 35 cm$^2$.

An insert may have asymmetry in its absorbent core (absorbent core asymmetry). Absorbent core asymmetry may result from arrangement of materials and features within the absorbent core to locate particular materials and features of the absorbent core where they are most needed and/or most effective, in accordance with features and functions of wearer anatomy as they differ front-to-rear.

For example, all or a portion of the rearward region 55 of insert 50 may include acquisition/distribution material 71 but less or no storage material 66 as compared with forward region 54, as may be seen by comparison of FIGS. 5A and 5B, 5C and 5D, and 5E and 5F, respectively. By this particular absorbent core asymmetry, storage material 66 may be located predominately in the front of the wearable absorbent article when worn. This may provide a predominate proportion of the insert's urine storage capacity closer to the urine exudation point of the wearer to reduce the likelihood of leakage, and remove potentially uncomfortable and/or unsightly size and bulk from between the wearer's legs or the wearer's backside area, particularly relevant when storage material 66 becomes swollen with absorbed liquid. Additionally, this particular asymmetry provides for economization of the amount of storage material 66 used, by locating it in only a portion of the insert rather than substantially along the entire insert. The liquid storage capacity of the forward region of the absorbent core may be greater than that of the rearward region of the absorbent core as measured by the Teabag Centrifuge Capacity test disclosed in U.S. Pat. No. 6,278,037. The liquid storage capacity of the forward region of the absorbent core may be at least about 10%, 20%, 50%, or even 100% or more greater than that of the rearward region. With such an arrangement, acquisition/distribution material 65 located in both forward and rearward regions 54, 55 can serve to acquire and move liquid (usually, urine) to the storage material 66 located predominately in the forward region 54. Alternatively, or additionally, the area and/or basis weight of the acquisition system or component materials in the forward region of the insert may be at least about 10%, 20%, 50%, or even 100% or more greater than that of the rearward region. Alternatively, or additionally, the surface area, cross-sectional area and/or lateral width of absorbent core 71 may be greater in the forward region 54 as compared with the rearward region 55. For example, the surface area, cross-sectional area and/or lateral width of absorbent core 71 may be greater in the forward region 54 as compared with the rearward region 55, to accommodate a greater proportion of the acquisition/distribution and/or storage material present in the forward region of the absorbent core.

Figure 5F:
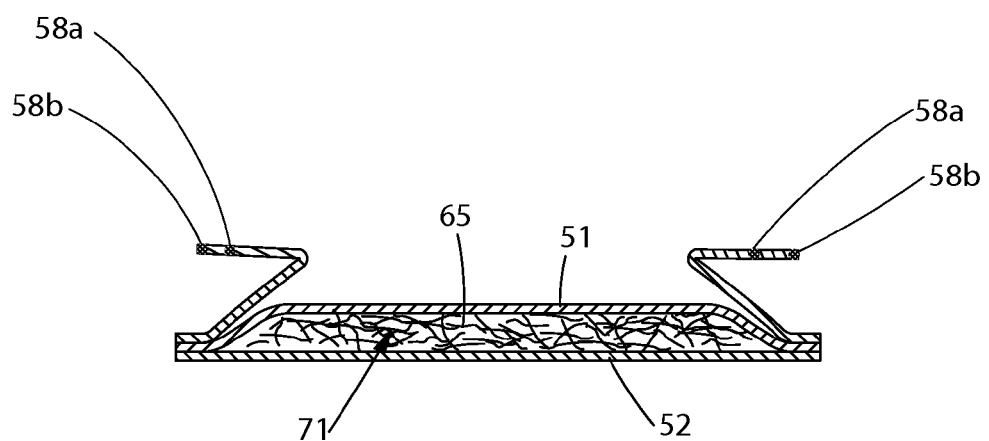
FIG. 5F is a cross sectional view of another example of an insert such as shown in FIG. 4, taken along line 5F-5F in FIG. 4.

Referring to FIGS. 5A, 5C and 5E, in other examples, absorbent material 66 in forward region 54 may be, respectively, dispersed within acquisition/distribution material 65 (FIG. 5A), contained within a separate liquid permeable structure or envelope 67 in fluid communication with acquisition/distribution material 65 (FIG. 5C); or dispersed on, or within an adherent matrix of, retaining material 68, and in fluid communication with acquisition/distribution material 65 (FIG. 5E). Conversely, the rearward region 55 may predominately contain acquisition/distribution material 65, but less storage material 66 as compared with forward region 54, or none (FIGS. 5B, 5D, 5F). Materials in forward region 54 also may be disposed according to construction described in one or more of co-pending U.S. application Ser. Nos. 12/141, 122; 12/141,124; 12/141,126; 12/141,128; 12/141,130; 12/141,132; 12/141,134; 12/141,141; 12/141,143; and 12/141,146, with a differing construction in rearward region 55.

In another example, storage material 66 and acquisition/distribution material 65 may occupying differing, distinct layers of absorbent core 71, as suggested by FIG. 5C. It may be desirable in some circumstances to make the layer containing acquisition/distribution material 65 larger in surface area (i.e., plan view surface area relative to the insert laid flat, as shown in FIG. 4) than the layer containing storage material 66, or vice versa. For example, if the layer containing acquisition/distribution material 65 is formed so as to have a larger surface area laterally across the insert in the forward region 54, this may serve to provide space for a greater quantity of acquisition/distribution material in the forward region. This may impart greater capacity in the forward region to rapidly absorb and distribute relatively large gushes of urine discharged toward the forward region, as may be desired for wearable absorbent articles for, e.g., older male babies and toddlers—enhancing containment capability of the insert.

In another example, however, such as for newborns and young babies, large gushes of urine might not be expected, but comparatively substantial quantities of liquid or low-viscosity fecal material may be. Thus, a wearable absorbent article for this group of intended wearers may include an acquisition/distribution layer of larger size, occupying a greater surface area, in the rearward region 55 of the insert. This may impart greater capacity in the rearward region to rapidly absorb gushes of liquid or low viscosity fecal material discharged toward the rearward region, and thereby enhance containment capability of the insert.

Differences between forward and rearward regions also may be included for purposes of sleep-use inserts. While an insert designed for awake-use may have the predominate proportion of its liquid-storage capacity in the forward region 54 as described above, an insert designed for sleep-use with, e.g., young babies, may have the predominate proportion of its liquid-storage capacity in the rearward region 55, to accommodate babies who sleep lying on their backs, by locating the predominate proportion of storage capacity where fluid exudates will flow under influence of gravity.

It also may be desired to dispose a thickening agent in the absorbent core in the rearward region 55 of the insert. A thickening agent may be useful for providing additional assurance that liquid or low viscosity fecal material will be thickened and thereby more immobilized, and more likely to be contained within the insert.

Insert 50 also may have overall shape/backsheet asymmetry. For example, viewed in a laid-flat position as shown in FIG. 4, insert 50 may occupy a larger surface area on one side of insert lateral axis 70 than on the other. This may be useful for purposes of comfort, body coverage, appearance, performance and/or economization in use of backsheet material(s). For example, in conjunction with including a predominate proportion of storage material 66, the forward region 54 of insert 50 may occupy a larger surface area, associated with a larger space within the insert to contain the storage material, e.g., an as to improve overnight absorption and containment capacity for wearers who sleep on their stomachs, and allow for the insert to remain flatter, particularly relevant when the absorbent material becomes swollen with absorbed liquid. Such larger surface area may be greater on one side of insert lateral axis 70 than the surface area occupied by the rearward region 55 on the other side of insert lateral axis 70.

Insert 50 also may have a narrowed region in the area which rests in the crotch region of the outer cover. This narrowing in the crotch region may serve to enhance wearer comfort by eliminating size and bulk between the legs. Referring to FIG. 2B, it may also serve to better enable the crotch region 26 of outer cover 20 to contain and maintain a laterally centered position of insert 50, by ensuring that insert 50, by having limited quantities of absorbent materials therein and limited width, does not swell beyond the space capacity of crotch region 26 of outer cover 20. Such narrowing may continue, for example, into the rear portion of the insert, thereby creating overall shape/backsheet asymmetry.

Insert 50 may also be asymmetrical across insert lateral axis 70 in other ways, to serve the same, related or other purposes as those described above.

It will be appreciated, therefore, that insert asymmetry across insert lateral axis 70 is a result of design and construction of the insert so as to have only one front region and only one rear region, i.e., the front and rear regions are not interchangeable, if the designed fit, comfort, performance and appearance of insert 50 are to be fully realized.

Grasp Structures

Referring to FIGS. 2G-2H, 3 and 4, insert 50 also may include respective forward and rearward user grasp structures 59, 61. User grasp structures 59, 61 may be provided to enable the user to quickly and easily grasp insert 50 proximate its respective ends.

Grasp structures as shown and/or suggested may enable the user to more quickly grasp and stretch insert 50 from a contracted position similar to that depicted in FIG. 3, to an extended position similar to that depicted in FIG. 4, which may be desirable for installing insert 50 into an outer cover. If user grasp structures 59, 61 are centered proximate to the respective ends of insert 50 as shown, this may also provide visual assistance to the user for co-locating respective centered fastener component pairs, described in more detail below.

Additionally, user grasp structures 59, 61 may serve to enable the user to quickly and easily grasp insert 50 proximate to its respective ends, which as a result of their distance from exudation points on a wearer's body, are less likely to be soiled at the time replacement of insert 50 becomes necessary or desirable. Thus, the user may be better enabled to avoid contacting the wearer's exudates with the user's hands when removing a soiled insert 50 from an outer cover 20.

Figure 2D:
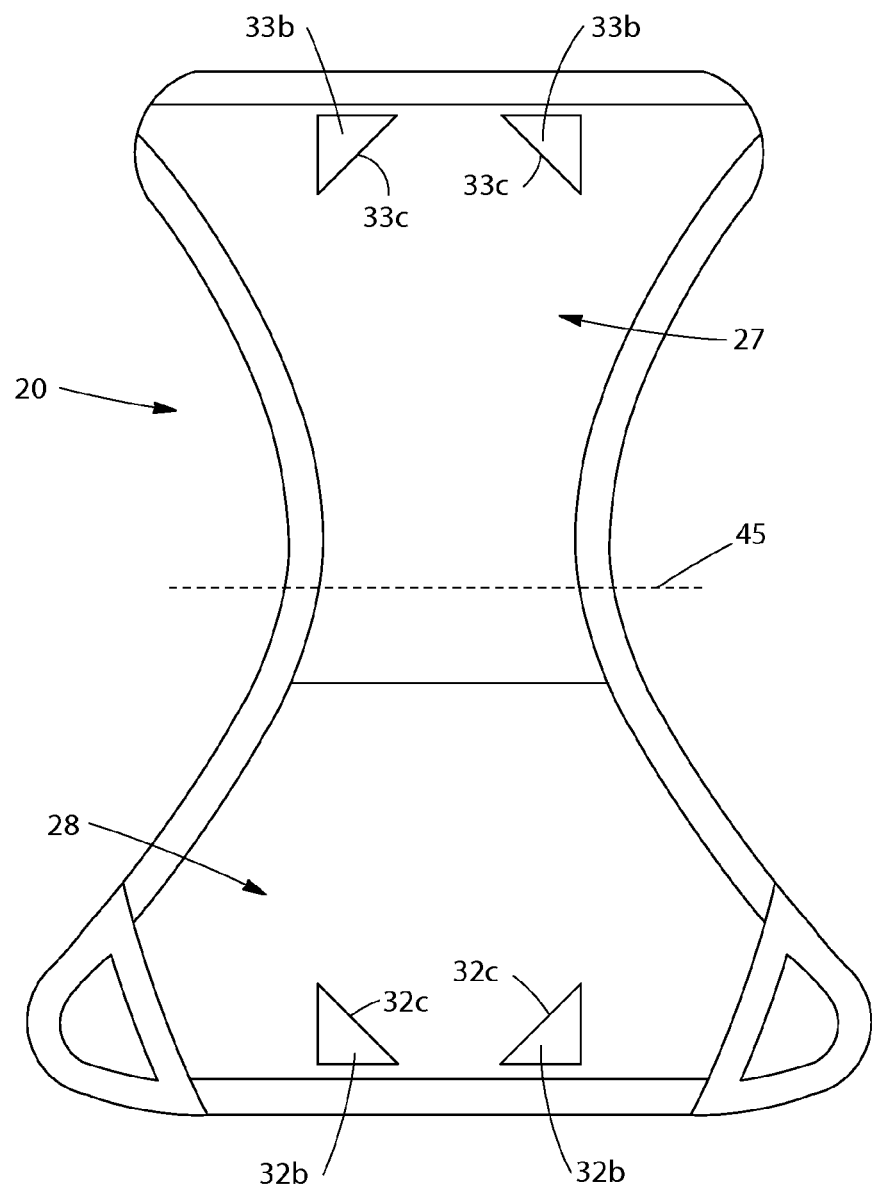
FIG. 2D is a plan view of an outer cover opened and laid flat, inner surface facing the viewer.
Figure 2E:
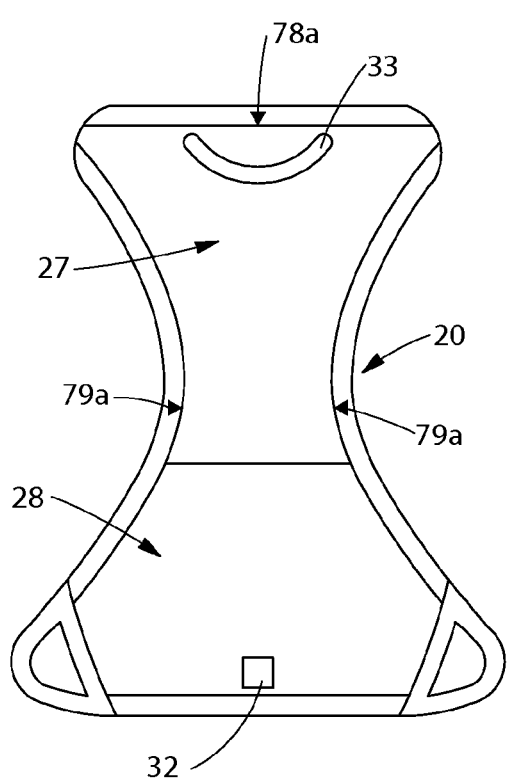
FIG. 2E is a plan view of an outer cover opened and laid flat, inner surface facing the viewer.
Figure 2F:
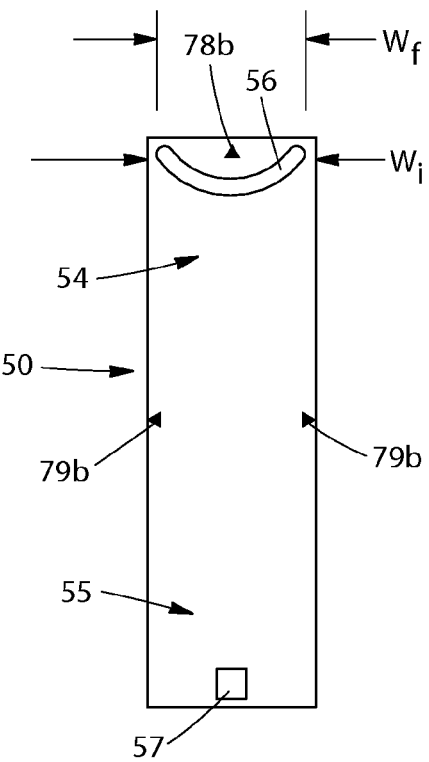
FIG. 2F is a plan view of an insert opened and laid flat, outer (garment facing) surface facing the viewer.
Figure 2G:
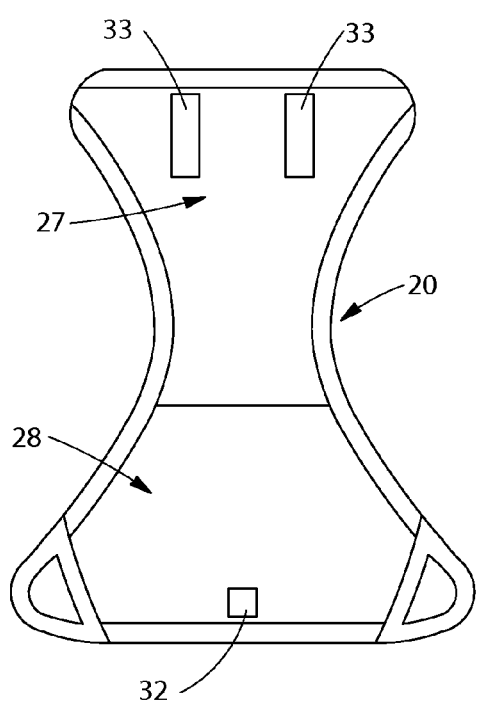
FIG. 2G is a plan view of an outer cover opened and laid flat, inner surface facing the viewer.
Figure 2H:
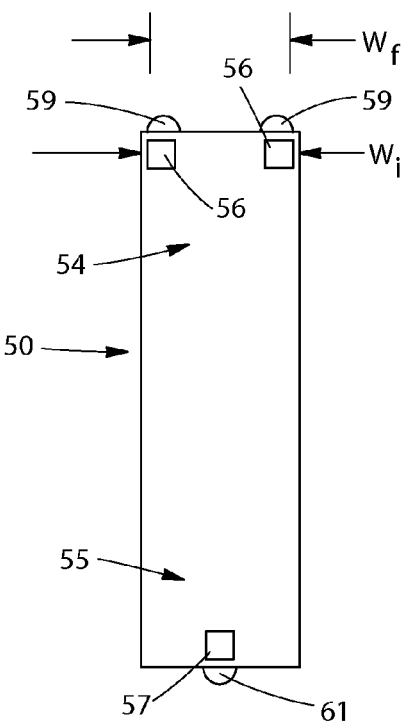
FIG. 2H is a plan view of an insert opened and laid flat, outer (garment-facing) surface facing the viewer.
Figure 2I:
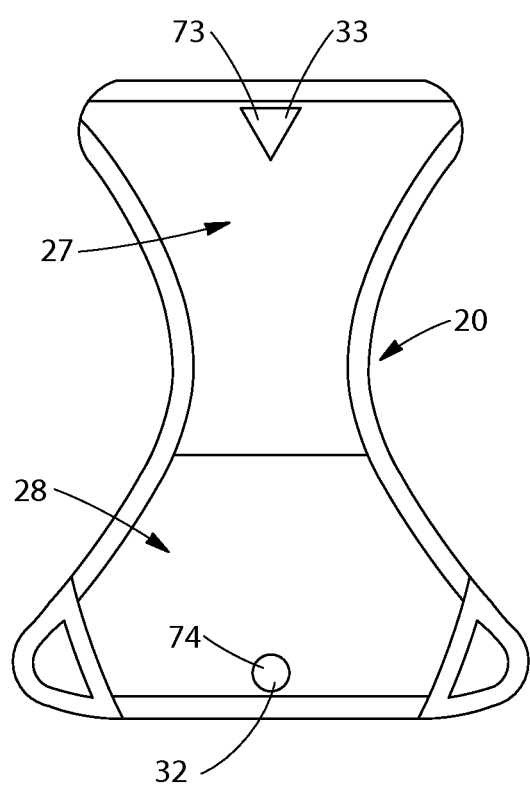
FIG. 2I is a plan view of an outer cover opened and laid flat, inner surface facing the viewer.
Figure 2J:
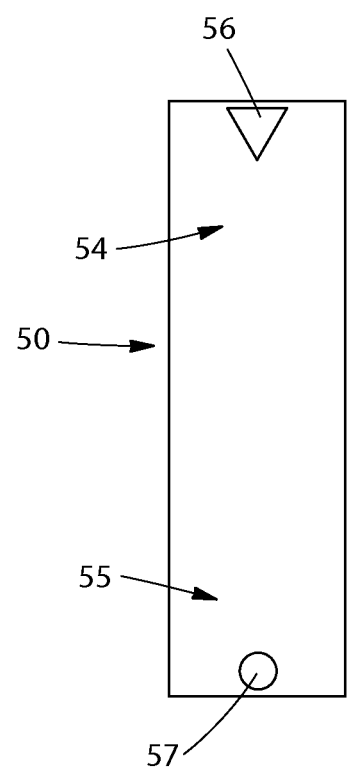
FIG. 2J is a plan view of an insert opened and laid flat, outer (garment-facing) surface facing the viewer.
Figure 2M:
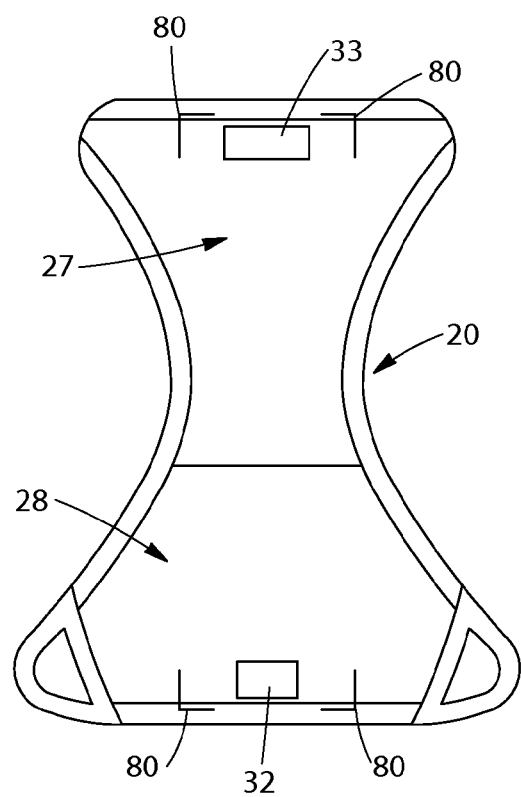
FIG. 2M is a plan view of an outer cover opened and laid flat, inner surface facing the viewer.
Figure 2N:
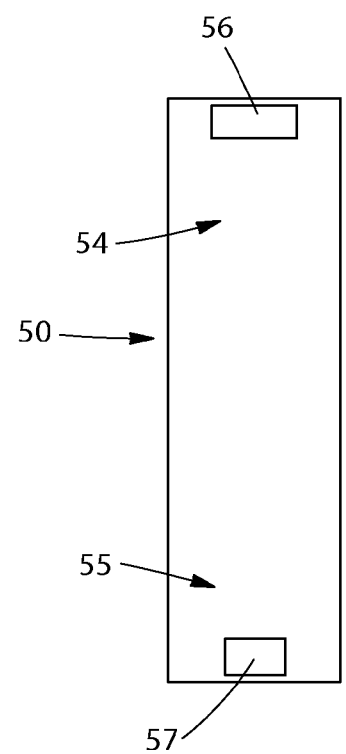
FIG. 2N is a plan view of an insert opened and laid flat, outer (garment-facing) surface facing the viewer.

Referring to the example depicted in FIGS. 2E-2F, it may be desirable in some circumstances to include more than one grasp structure 59 on the insert. This may be deemed useful in examples such as depicted in FIGS. 2E-2F, where more than one fastener component 56 is disposed on an end of an insert. In such circumstances, including a separate grasp structure 59 associated with and proximate to each fastener component 56 may enable a user to manipulate portions of an insert to more easily accurately locate and install it within an outer cover with fastener components 59, 33 suitably co-located and/or aligned. It may also enable a user to more easily tug the fastener components 56 away from paired fastener components 33 to separate them, when it is necessary to remove the insert from the outer cover, by localizing or focusing the user's tugging forces where they are needed to effect such separation.

User grasp structures 59, 61 may include tab-like extensions as shown in FIGS. 2E-2F, 3 and 4, with free ends unattached to the outer cover 20 when insert 50 is installed therein, which are easily graspable. User grasp structures may have different forms as well. By way of non-limiting example, user grasp structures may take the form of loop-like extensions (not shown) extending from the ends of insert 50, finger holes (not shown) through insert 50 proximate the ends thereof, pockets with openings facing the lateral centerline 70 of the insert, and other structures that facilitate grasping and pulling of insert 50 at locations proximate to its ends.

Additionally, grasp structures 59, 61 may be formed of materials having a high coefficient of friction (e.g., at least about 0.5), resiliently compressible materials and/or surfaces having three-dimensional relief, to facilitate secure gripping and pulling the insert by the user.

Grasp structures 59, 61 also may be configured or adapted so as can be folded over or under the respective ends of insert, toward the lateral centerline of the insert. This can serve to conceal the grasp structures behind other materials and protect them from contamination by bodily exudates. Alternatively or in addition, it can serve to add convenience for the user.

Insert/Outer Cover Fastener Components; Orientation Indicia; Other Possible Features Referring back to FIGS. 2B, 3 and 4, as previously noted, outer cover 20 may have one or more insert fastener components such as front and/or rear insert fastener components 33, 32 disposed thereon. Insert 50 may have front and/or rear fastener components 56, 57 disposed thereon. Respective front and/or rear fastener components 56, 57 on insert 50 may be selected and/or adapted to be cooperative to enable fastening with respective front and/or rear insert fastener components 33, 32 disposed on outer cover 20.

Types, Locations and Localization of Fastening Locations

In one example, to enable fastening of respective front and rear fastener components 56, 57 of insert 50 with respective front and rear insert fastener components 33, 32 on outer cover 20, respective fastening pairs 56, 33 and 57, 32 may include cooperating fastener components. An example of a suitable hook-and-loop fastening system is a VELCRO system, a product of Velcro Industries B.V., components of which are available from Velcro USA, Inc., Manchester. N.H. A hook-and-loop fastening system provides certain advantages. Because the respective hook and loop components are supplied in sheet or strip form, they may be cut into suitably shaped patches that can be affixed to a cloth substrate by various mechanisms, including adhesive bonding, mechanical bonding, ultrasonic bonding, sewing, stitching, serging, edging, and the like. If respective hook-and-loop patches are used as fastener components, relative ease of fastening, simplicity and convenience for the user (as compared with, for example, fastener components such as a button and button hole) are one among several advantages provided, because fastening is effected simply by placing the fastener components in face-to-face contact and applying gentle pressure.

Some types of hook components may, in some circumstances, tend to snag or catch undesirably on a variety of materials in addition to intended corresponding loop components, while most types of loop components currently available do not have this tendency. Thus, in some circumstances it may be desired that patches of loop components form one or both of insert fastener components 33, 32, while patches of hook components form one or both of fastener components 56, 57. This arrangement places a non-snagging insert fastener component on the outer cover. This may be desirable in some circumstances, such as when the outer cover 20 is designed to be reusable—reducing the likelihood that components on an outer cover 20 will undesirably snag on other parts of outer cover 20 or on other articles, such as clothing articles, being stored or laundered along with outer cover 20.

However, fastening pairs 56, 33 and 57, 32 need not necessarily include respective components of a hook-and-loop fastening system, and need not necessarily include respective components of a two-component fastening system. Rather, a fastening system may require only one fastener component, or use other types of fastener components. Fastener components used may be adapted to engage, retain, and otherwise hold the insert or a portion thereof. A fastener component on outer cover 20 may include a patch of adhesive; a structure having a region of relatively high coefficient of friction; a pocket; flap; strap; or other capturing, holding and/or retaining surface, device or structure. Thus, referring to FIG. 2C in one example, the inside of outer cover 20 may include one or more pocket structures 32*a*, 33*a* situated on or along the inner surface 25 of outer cover 20, in, e.g., the front region 27 or rear region 28. Such a pocket structure may have an opening facing downward or upward (relative to the wearer in a standing position, and relative to FIG. 2B). A pocket structure may be adapted to receive, fit and capture, for example, the forward edge and a portion of forward region 54 of insert 50. A pocket structure 33*a*, 33*b* may have an opening facing lateral axis 45, such that an end of insert 50 may be inserted therein and retained thereby. A pocket structure may alternatively have an opening facing away from lateral axis 45, such that an end of insert 50 may be inserted therein and retained thereby, and then insert 50 may be folded back over such opening and toward lateral axis 45. Referring to FIG. 2D, in another example, one or more pockets 32*b*, 33*b* may be provided in the front and/or back region on the inner surface of the outer cover 20 positioned such that a corner of an insert 50 may be inserted into and retained by the pocket. Such pockets may have respective openings defined by edges of material 32*c*, 33*c* forming an angle with respect to both the lateral and longitudinal axes of between about 0 and 90 degrees, but more preferably, between about 30 degrees and 60 degrees. One or more of such fastener components may be provided in lieu of, in addition to, or in combination with, other fastener components disposed at the front region of the outer cover 20 and forward region of insert 50. As one example, an outer cover 20 may have a pocket structure 33*a* in front region 27 (see FIG. 2C) in combination with a patch of loops component forming rear fastener component 32 (see FIG. 2B). With such a structure and a suitably adapted insert 50 having a patch of hooks as fastener component 57, to install the insert the user may insert the forward edge of insert 50 into the pocket structure 33*a*, and then fasten the rearward portion of insert 50 into the rear region of the outer cover 20 by engaging respective fastener components 32, 57.

In another example, fastener components 32, 33 may be respective patches of hook components, while fastener components 56, 57 may simply be surfaces formed of woven or nonwoven material adapted to be attachably engageable by such hook components. In yet another example, fastener components 56, 57 may include respective patches of hook components, while fastener components 32, 33 may simply be surfaces formed of woven or nonwoven material suitable for, or adapted to be, attachably engageable by such hook components.

Also, a fastener component in any form, including a respective component of a fastening pair 56, 33 and 57, 32 may be disposed on either of insert 50 or outer cover 20. For example, a hook patch may be disposed on either of insert 50 or outer cover 20, with a cooperating loop patch disposed on the other of insert 50 or outer cover 20.

An insert fastener component such as component 32 on outer cover 20 may be attached or connected to at least a portion of an anchoring system, such as an anchoring band 38, or diagonal anchoring band 38a. This may provide, as one advantage, the distribution of structural loading resulting from the weight of absorbed or contained exudates, as described in one or more of the patent applications cited above, in the description of anchoring bands.

Fastening locations may be multiply disposed, for example, at each of the four corners of insert 50 and corresponding locations on outer cover 20, and even at other locations along insert 50 and outer cover 20, created by fastener components suitably selected and disposed. For example, fastener components may be disposed along the longitudinal sides proximate the ends of the insert in the forward and/or rearward region of the insert. Fastener components may be disposed adjacent an edge of the insert, or may be disposed laterally and longitudinally inboard of the edge. For example, a fastener component may be disposed at least 1, 2, or 3 cm from all edges of the insert. In certain embodiments, at least one fastener component is disposed at least a distance from the lateral or longitudinal edge, or both, of the insert equivalent to one-fourth the width of the insert. In one embodiment, a fastener component is disposed along at least about one-fifth of the length of the longitudinal axis.

In another example, a fastening system such as either of fastener component pairs 56, 33 and 57, 32 may form a singularized and localized fastening location proximate each of, or either, the forward/front and/or rearward/rear ends/regions as suggested in the Figures. Having only two respectively singularized, localized fastening locations substantially laterally centered on the insert and the outer cover, as suggested in FIGS. 2B and 3, provides an advantage of simplicity and ease of installation for the user, by presenting only two locations at which the user must co-locate and fasten insert 50 to outer cover 20.

Additionally, having a single, localized fastening location proximate only one or two ends of insert 50, such as suggested in FIGS. 2B and 3, provides a partially force-decoupled attachment of insert 50 within outer cover 20. This may be especially desired in the rear region 28 of outer cover 20, where extensibility and/or elasticity of outer cover 20 may be especially desired to maintain fit, comfort and appearance while accommodating body contours and movements of the wearer about the buttocks and hips. With this force-decoupled arrangement, the portions of outer cover 20 surrounding fastening element(s) 33, 32, such as waistband portions 34, 35, and front and rear regions 27, 28, may laterally stretch and contract substantially independently of and unimpeded by the structure of insert 50 and portions thereof. This may avoid lateral bunching of the ends of insert 50 with lateral contraction of the outer cover 20, and/or, conversely, may avoid having the structure of insert 50 restrict outer cover 20 from stretching or contracting laterally, as a result of a more force-coupled arrangement therebetween. Such lateral bunching or restricting otherwise may be incidental to fastening insert 50 within outer cover 20 in a manner that force-couples a greater portion of the width of insert 50 to outer cover 20, e.g. by use of more than one fastening location across the width of insert 50 proximate a given longitudinal location, or by use of a laterally delocalized/extended continuous fastening location along a larger portion of the width of insert 50. Force-decoupling, therefore, may provide for enhancement of fit, appearance and wearer comfort, as well as improved capability for maintenance of intended insert shape and performance while worn.

Thus, in one example, referring to FIG. 4, a patch of hook components forming a fastener component 56 and/or 57 attached to insert 50 may be substantially laterally centered on the insert as suggested in the figure, and may have an width $W_f$ attached along insert 50 that extends no more than about 50% of the lateral width $W_i$ of the insert 50 at forward region 54 and/or rearward region 55. This provides that no more than about 50% of the width of the insert 50 at, e.g., forward region 54 and/or rearward region 55, will be force-coupled to the outer cover by operation of the patch of hook components, and that, correspondingly, about 50% of such width (i.e., that portion of width $W_i$ that is not attached to, or force-coupled to, the insert along width $W_f$) is force-decoupled from the outer cover 20 when insert 50 is installed therein. In some circumstances, it may be desired that the portion of the lateral width of forward region 54 and/or, especially, of rearward region 55 of insert 50 that is force-decoupled from the outer cover is even greater than about 50%. Thus, it may be desired that the width $W_f$ of a fastener component 56 or 57, comprising, e.g., a continuously attached patch of hooks, is no more than about 40%, no more than about 30%, or even no more than about 20%, of the lateral width $W_i$ of the insert at the region where the fastener component is situated. In another example, it may be desired in some circumstances that at least about 50% of the lateral width of the insert 50 in the front and/or rear region 54, 55, is force-decoupled from the outer cover. In some circumstances it may be desired that more than about 50%, more than about 60%, more than about 70%, or even more than about 80%, of the lateral width of the insert at any longitudinal location, is force-decoupled from the outer cover when installed therein.

As depicted in FIGS. 2E-2F and 2G-2H, examples are contemplated wherein singularized/localized force-decoupled fastener component pairs 32, 57 may be employed in the rear region 28 of the outer cover 20 and rearward region 55 of the insert 50, while fastener component pairs 33, 56 effectively controlling the forward corners of the insert 50 may be employed in the front region 27 of the outer cover 20 and forward region 54 of the insert 50. This may allow force decoupling of the stretchable outer cover in the back of the article, while maintaining control over the front corners of the insert.

Other fastener components that provide such singularized and relatively laterally localized fastening locations, providing limited force-coupling across the lateral width of at least one end of insert 50, are possible. Other suitable fastener components may include tab and slot fasteners, macro hook and loop fasteners, button fasteners, interlocking fasteners, hook and slot fasteners, snap fasteners and other fastener types available.

In some insert embodiments, as implied above, the corners of the insert 50 when in use may be prone to buckling, sagging or rotating toward the insert lateral axis 70, or out of the contour of the body of the insert, in response to forces resulting from wearer motion or position, or exudate loading, e.g., in the crotch region. Also, referring to FIG. 3, and from the description of standing cuffs 53 with cuff elastics 58a, 58b set forth above, it can be appreciated that, if longitudinal tensile forces are imparted by pre-strained cuff elastics 58a, 58b, standing cuffs 53 may tend to pull the respective outer corners of insert 50 longitudinally toward each other. If there is not structure present to resist these forces, the outer corners of insert 50 may sag or buckle, and standing cuffs 53 may be loosened, sag or even collapse. This may lead to gaps between the edges 58 of the cuffs and the wearer's body. In turn, this may compromise the cuffs' gasketing function, and increase the risk of leakage.

While it may be important at both ends of the insert, control of the insert corners may be particularly important in the forward region 54, due to its closer proximity to the urethra. Insert designs in which exuded urine is predominately stored in the forward region also may concentrate the weight and expansion stress of exudate loading in the forward region 56, and thus, on the forward corners of the insert 50.

Control of the corners to reduce the likelihood of such sagging and rotation may be improved, in one group of examples, by placement and/or shaping of fastener component pairs. Referring again to FIGS. 2E-2F and 2E-2F, it can be seen that fastening component pairs 33, 56 in, e.g., the respective front/forward regions of the outer cover 20 and insert 50 may be arranged, shaped, sized and/or placed such that the forward corners of insert 50 are effectively captured and held to the outer cover 20 when insert 50 is installed therein. The fastener component(s) 56 disposed on the insert may, accordingly, have a width $W_f$ at least equal to about one-fourth, or one-half, of the width of the insert. In some examples, the width $W_f$ of the fastener component(s) may be between about 50% and 100%, or between about 75% and 100%, or even between about 85% and 100% of the width $W_i$ of the insert (not including cuffs 53). If multiple fastener components 56 are included, e.g., in a line, array, or other pattern, the fastener component width is considered to be the lateral distance between the outermost edges of the fastener components 56.

Insert End Support Stiffeners

In some circumstances, inclusion of fastening component pairs which attach the outer corners of the insert to the outer cover may be undesirable for reasons of cost and/or complexity, or may sacrifice the advantages of having only one singularized/localized fastening location proximate each end of insert 50, as described above. Particularly in the rear region of the outer cover 28, a singularized and relatively localized fastening location providing a force-decoupled arrangement may be desirable, for the reasons described above.

In this circumstance, it may be desirable to include a stiffening component proximate to one or both ends of the insert, but especially an end adapted with a singularized and relatively localized fastening location providing a force-decoupled arrangement. Referring to FIGS. 3 and 4, end support stiffeners 60 and 62 may be included. Such end support stiffeners may serve to aid the user in engaging the insert with the outer cover, and to help insert 50 maintain its intended shape and configuration while being worn beneath an outer cover, i.e., help maintain the intended position and gasketing function of the standing cuffs 53. End support stiffeners 60, 62 also may help control the corners of the insert regardless of the size, type or location of fastener components included on the insert. In addition to providing resistance to longitudinal pull of cuff edges 58, end support stiffeners 60, 62 may provide resistance to bending in any direction or plane.

End support stiffeners 60, 62 may be affixed to, or incorporated within, insert 50 proximate the ends thereof as suggested by FIGS. 3 and 4. In addition to increasing the tendency of insert 50 to maintain optimal shape while in use, such end support stiffeners may increase the tendency of the respective ends of insert 50 to stay open and flat before insert 50 is installed in an outer cover. Because the ends of insert 50 may otherwise be folded over or bunched while being stored and/or carried by the user before installation, end support stiffeners may enhance user convenience, by causing the ends of insert 50 to maintain or seek a shape/configuration that requires less manipulation by the user to install it in an outer cover.

Referring to FIG. 4, one or more end support stiffeners 60, 62 may be disposed in a lateral orientation with respect to the insert and formed of any flat, sheet-like or card-like material, or any flat, stiffened assembly. In one example, an end support stiffener may be formed by folding over a portion of the insert end material(s) to create a stiffened region comprising folded layers of material. In another example, end support stiffeners 60, 62 may be formed by depositing onto the ends of insert 50 lateral bands, strips or other shapes or patterns of deposits of liquid or semi-liquid adhesive or other material that cures or cools to a stiffened state, and thereby imparts added stiffness to the substrate to which it is applied. In another example, end support stiffeners may be formed of cardboard or like material. One example of suitable stiffener material is 0.031 in. thick VOLARA foam supplied in sheet form (a product of Sekisui Voltek, LLC, Lawrence, Mass.). Stiffener materials may be laminated with or adhesively applied to portions of insert 50 to be stiffened, or applied, affixed or included by any other suitable method. Other examples of suitable stiffening materials may include added layers of nonwovens, tufted nonwovens, films, laminates of films and nonwovens, patches of fastener loops or hooks components, portions of a suitable grasp structure, etc.

It may be desired that the portions of insert 50 including one or more end support stiffeners 60, 62 are sufficiently stiff to effectively resist the tension forces in standing cuffs 53 and substantially maintain standing cuffs 53 in their gasketing configurations while insert 50 is in use, and substantially maintain the corners of insert 50 in laterally extended positions, preventing buckling or bunching of the same. The amount of stiffness desired may depend upon various factors including the inherent stiffness of the insert materials without a supplemental end support stiffener, and the amount and/or range of tension in the standing cuffs when the article is worn. At the same time, for purposes of wearer comfort and safety, it may be desirable that the portions of the insert including the one or more end support stiffeners 60, 62 are pliable enough to flex comfortably with the wearer's body movements, and to collapse before any form of contusion or impalement injury hazard would be presented. It also may be desirable that stiffened portions are elastic in nature, in they will tend to return to a substantially flat configuration after being bent, folded or twisted.

End support stiffeners 60, 62 may increase planar, lateral and/or longitudinal stiffness of the areas of insert 50 in which they are located, as compared with portions of the insert adjacent such stiffeners with respect to a plan view (such as FIG. 4). These differing orientational aspects of stiffness may affect various attributes of the insert. For example, referring to FIG. 3, it can be seen that the ability of a portion including an end support stiffener 60, 62 (stiffened portion) to resist longitudinal tension forces in standing cuffs 53, may be affected by one or more of planar and longitudinal stiffness of the stiffener. The pliability and relative comfort or discomfort for the wearer, associated with a presence of a stiffened portion, may be affected by planar stiffness of the stiffener.

One measure of stiffness relevant to the ability of a stiffened portion to resist longitudinal tension forces in standing cuffs is Edge Deflection Force, which is measured according to the Edge Deflection Force Measurement Method set forth below. In view of the potentially competing objectives of structural rigidity and comfort, it may be desired that a stiffened portion of an insert end, i.e., the portion of an end that includes an end support stiffener, have an average Edge Deflection Force from 0.2 N to 3.0 N, or from 0.4 N to 2.0 N, or even from 0.50 N to 1.70 N, as measured by the Edge Deflection Force Measurement Method set forth below.

Another measure of stiffness relevant to the comfort of a stiffened portion is the Peak Bending Force and Bending Stiffness, which are measured according to the Bending Stiffness Measurement Method set forth below. In view of concerns for comfort, it may be desired that a stiffened portion of a an insert end, i.e., the portion of an end that includes an end support stiffener, have an average Peak Bending Force of no more than 4.0 N, or even no more than 3.7 N, and an average Bending Stiffness of no more than 675 N/mm, or even no more than 630 N/mm.

End support stiffeners 60, 62 may be located adjacent or near one or both ends of insert 50 and may extend laterally from the lateral center thereof to stiffen the insert along a substantial portion of its width. Alternatively, the stiffeners may be located at least about 0.5, 1, or 2 cm from the end of insert 50, and may be substantially centered about the longitudinal center line of the insert. The one or more end support stiffeners may have a width of from about 50% to about 100% of the lateral width of the insert, or may extend beyond the longitudinal edges of other materials forming the insert. The end support stiffeners may have any longitudinal dimension, although, in some circumstances, a longitudinal dimension less than 25% of the insert length may better assure comfort for the wearer, and therefore, may be desired. In some examples, the longitudinal dimension of an end support stiffener may range from about 5 mm to about 50 mm. A stiffener also may extend longitudinally beyond the lateral edge of other materials forming the insert. One or both ends of the insert may include an end support stiffener. In examples wherein the insert comprises more than one end support stiffener, the respective end support stiffeners may have differing shapes, dimensions, stiffness, thickness, color, structure, placement, material(s) or composition. An end support stiffener also may include, or be integral with, a grasp structure or fastener component as described above, and as suggested in FIG. 3 (end support stiffener 60 is depicted as integral with grasp structure 59).

Targeting, Orientation and Alignment Indicia

As discussed above, an insert 50 may be imparted with features that make it asymmetric about its lateral axis. Despite such asymmetrical configuration, as suggested by FIG. 4, insert 50 may have an overall profile that does not appear to be asymmetric about its lateral axis. For example, as depicted in FIG. 4, insert 50 may have an overall profile, when opened and laid flat, that is substantially rectangular, and thus, appears to be symmetric about its lateral axis 70. Other insert profiles are possible as well, which have overall profiles which appear symmetric about a lateral axis. Additionally, even where an insert 50 has an overall profile that is asymmetric about its lateral axis, it may not be clear just from the profile which portion is the forward portion and which portion is the rearward portion. Thus, absent a sufficiently perceptible signal indicating which portion of the insert is the forward portion and which is the rearward portion, a user may have difficulty determining the same, and as a result, may attempt to install an insert into an outer cover with incorrect relative front-rear orientation—in turn, resulting in sub-optimal fit, appearance, exudate containment and/or comfort.

The insert and/or outer cover may comprise one or more insert targeting indicia to indicate, facilitate and/or compel correct positioning and association of portions of the insert within the outer cover. The insert targeting indicia may comprise verbal or non-verbal instructive indicia, visual targeting indicia, cooperating geometrical features, cooperating types of fastener components, or cooperating designs of fastener components sized and formed to indicate or compel the engagement of the insert with the correct region of, and in correct orientation with, the outer cover so as to enable the optimum performance of the wearable absorbent article. Other examples of possible targeting indicia components include one or more cooperating colors, shapes, patterns, lines, outlines, silhouettes, other geometrical features, protrusions or depressions, textures, patterns, targeting lines or crosshairs, bulls-eye representations, and the like, disposed on the outer cover and/or the insert to indicate correct positioning of the insert within the outer cover. In one example, the inner surface of the outer cover may be imprinted with an outline of an insert, or a silhouette of an insert. Alternatively, one or both of the forward and rearward regions 54, 55 of the insert may have disposed thereon a pictogram showing the outer cover shape, or a generalized version thereof, with the front and back of the outer cover indicated via size, color, contrast, or some other indicator, showing the correct insert installation orientation. For example, an outer cover pictogram disposed in the rearward region 55 of the insert may have the rear outer cover region, or portions thereof, indicated with a brighter color, an arrow, a circle, etc., while an outer cover pictogram disposed in the forward region 54 of the insert may have the front outer cover region, or portions thereof, indicated similarly.

Targeting indicia also may comprise at least two cooperating components, one on the outer cover 20 and one on insert 50, such that when these two components are associated, the respective components of outer cover/insert system will be properly oriented with respect to one another and will perform most optimally. In one example, the inner surface of the outer cover may be imprinted with a first arrow pointing at an insert location, and the insert may be imprinted with a second arrow pointing at the first arrow when the insert and outer cover are correctly relatively positioned.

Indicia may be cognitively correlating, or non-correlating, a correlation indicating a correct optimal placement, and a non-correlation indicating an incorrect sub-optimal placement. Respective cognitively correlating targeting indicia may include an indicium on the outer cover that cognitively correlates with an indicium on the insert, indicating to the user the correct relative positioning and engagement of the insert and the outer cover. For example, respective cognitively correlating indicia on the insert and outer cover may have a common color, shape, or texture. (As used herein, "common color" includes any first color and recognizable shades or variants thereof, which in view of all features of the article is visibly and cognitively distinguishable from another color on the article.)

Referring to FIGS. 2B, 3 and 4, when an insert 50 is asymmetrical as described above, it may have only one optimal forward region 54 and only one optimal rearward region 55. Similarly, when an outer cover 20 is asymmetrical as described above, it may have only one optimal front region 27 and only one optimal rear region 28. Thus, in the event either or both of these asymmetries are substantial, installation of insert 50 into outer cover 20 with incorrect relative front-rear orientation may cause the wearable absorbent article not to fit and/or function optimally. Accordingly, it may be desirable in some circumstances to incorporate one or more indicia into the outer cover 20 and/or insert 50 that are adapted to inform the user as to the correct respective front-rear orientation of these components. Such indicia may provide such information to the user functionally, tactilely and/or visually.

Functional indicia may include fastener components that function properly, effectively and/or optimally with correct front-rear orientation, but do not function properly, effectively and/or optimally with incorrect front-rear orientation.

For example, referring to FIGS. 2B and 3, front insert fastener component 33 on outer cover 20 may be cooperative to effect optimal/maximum fastening security only with front fastener component 56 on insert 50, but not with rear fastener component 57 on insert 50. Similarly, rear insert fastener component 32 on outer cover 20 may be cooperative to effect optimal/maximum fastening security only with rear fastener component 57 on insert 50, but not with front fastener component 56 on insert 50.

In a more specific example conceptually appreciated from FIGS. 2K-2L, front insert fastener component 33 on outer cover 20 may include a patch of loops, while front fastener component 56 on insert 50 may include a mating patch of hooks (mating relationship indicated by hatching of components 33, 56 in FIGS. 2K-2L). Correspondingly, rear insert fastener component 32 on outer cover 20 may include a patch of hooks, while rear fastener component 57 on insert 50 may include a mating patch of loops (mating relationship indicated by absence of hatching of components 32, 57 in FIGS. 2K-2L). Thus, in this particular example, if a user mistakenly attempts to fasten rear fastener component 57 on insert 50 (loops) to front insert fastener component 33 on outer cover 20 (loops), proper or optimal fastening will not be effected, which will communicate to the user that he/she must rotate insert 50 by 180 degrees to install it with correct/optimal front-rear orientation on the outer cover.

In another specific example also conceptually appreciated from FIGS. 2K-2L, front insert fastener component 33 on outer cover 20 may include a female snap fastener component, while front fastener component 56 on insert 50 may include a mating male snap fastener component (mating relationship indicated by hatching of components 33, 56 in FIGS. 2K-2L). Correspondingly, rear insert fastener component 32 on outer cover 20 may include a male snap fastener component, while rear fastener component 57 on insert 50 may include a mating female snap fastener component (mating relationship indicated by absence of hatching of components 32, 57 in FIGS. 2K-2L). Thus, in this particular example, if a user mistakenly attempts to fasten rear fastener component 57 on insert 50 (female snap fastener component) to front insert fastener component 33 on outer cover 20 (female snap fastener component), the components will not fit properly together and proper/optimal fastening will not be effected, which will communicate to the user that he/she must rotate insert 50 by 180 degrees to install it with correct/optimal front-rear orientation.

Thus, functional indicia may include any fastener components that will function properly and/or optimally to effect fastening and maximum fastening security between insert 50 and outer cover 20 when the two are properly oriented, but will not function properly or optimally otherwise. Any different types of fastener components or systems may be combined to differentiate the forward and rearward regions of the insert and indicate correct orientation within the outer cover. Generally, with the use such functional indicia, the fastener components types in the forward region of the insert and front region of the outer cover are respectively incompatible, or significantly less effective, with the respective fastener components types in the rearward region of the insert and rear region of the outer cover. As another example of such functional indicia, the front insert fastener pair 33, 56 may be a hook and loop fastening system, while the rear insert fastener pair 32, 57 may be a snap fastening system. In another example, the front insert fastening component(s) may include a pocket or flap structure, while the rear fastening components embody a dissimilar fastening system. The front and rear insert fastening systems may comprise any two different fastening systems as disclosed herein, or as otherwise available.

In another example, functional indicia may be embodied by fastener pairs 33, 56 and 32, 57 having mutually exclusive geometries of similar or compatible fastening system types. For example, as depicted in FIGS. 2E-2F and 2G-2H, the front fastener pair 33, 56 may have a first placement and geometry, while the rear fastener pair 32, 57 may have a second placement and geometry, such that if installation of insert 50 within outer cover 20 with incorrect front-rear orientation is attempted, the fastener pairs will not align to provide visibly correct and functionally effective attachment, communicating to the user that that he/she must rotate insert 50 by 180 degrees to install it with correct/optimal front-rear orientation. In another similar example (not depicted), the front insert fastening system may have an open circle, or doughnut-like, geometry, while the rear insert fastening system may have a geometry of a circle with a diameter less than that of the central opening in the open circle of the front insert fastening system. In yet another example (not depicted), the front and rear insert fastening systems may be located primarily on one side of the longitudinal axis of the article (i.e., the longitudinal axes of both the insert and the outer cover). In this example, if the insert is applied to the outer cover in the incorrect front-to-back orientation, the insert fastening components and fastening components will not align correctly. In another example (not depicted), the front insert fastening system may comprise an interlocking fastener oriented along the direction of the longitudinal axis of the article, while the rear fastening system may comprise an interlocking fastener oriented along the direction of a waist edge or lateral axis of the article. In another example which may be conceptually appreciated from FIGS. 2E-2F, the front fastening system may include one or more fastening components 33, 56 disposed along the longitudinal edges of the insert, while the rear fastening system may include a single fastening pair 32, 57 having a width less than the insert width and disposed on the longitudinal axis of the article.

Functional indicia need not necessarily be limited to fastener components. Functional indicia also may be embodied in other features of the outer cover and insert that affect how the two fit or function together in correct, optimal front-rear orientation versus incorrect (reverse), sub-optimal front-rear orientation. Thus, functional indicia may additionally be associated with or combined with another functional element of the outer cover or insert. Indicia may be associated with elements of the outer cover such as a waistband, side panel, stretch element, leg cuff, physical retention fastener component (e.g., a pocket or retaining strap), and the like. Indicia may be associated with elements of the insert, such as a waist cap, waist band, standing cuff, fecal management feature, insert positioning aid, insert stiffening aid, insert removal aid, or insert disposal aid.

From the foregoing it will be appreciated that other forms of functional orientation indicia are possible, within the principle of the foregoing description. Additionally, any of the differing types of indicia described may be included in a single article, in any combination.

In other possible examples, instead of respective functionally cooperative/uncooperative pairs of components as described above, insert 50 and outer cover 20 may include respective non-functional indicia, such as tactile or other sensory indicia.

For example, the front insert and outer cover fastener components may be selected or formed so as to have a first tactile attribute, while the rear insert and outer cover components may be selected or formed so as to have a second tactile attribute. In another example, features of the insert and outer cover may have features such as 3-dimensional shapes that are mating or geometrically cooperating with optimal front-rear orientation, but not mating or geometrically cooperating with reversed, suboptimal front-rear orientation.

In other possible examples, instead of or in addition to respective functionally cooperative/uncooperative pairs of fastener components or tactile indicia components as described above, insert 50 and outer cover 20 may include respective visual indicia. Outer cover 20 may include respective front and rear visual indicia 73, 74 disposed on the front region 27 and rear region 28, respectively. Respective visual indicia disposed on insert 50 and outer cover 20 may be adapted to provide a visual cue to the user of correct/optimal orientation and placement of insert 50 within outer cover 20.

For example, components of visual indicia and a visual cue may involve use of a common color. In one particular example, front and/or rear visual indicia 73, 74 disposed on outer cover 20 may comprise respective common colors visibly distinct from one another. (As used herein, "common color" includes any first color and recognizable shades or variants thereof, which in view of all features of the article is visibly and cognitively distinguishable from another color on the article.) Insert 50 may have respective cooperating indicia disposed or embodied thereon. Thus, for example, forward and rearward user grasp structures 59, 61 on insert 50 may bear or be colored with colors respectively common and corresponding with those comprised by front and/or rear visual indicia 73, 74. More particularly, for example, front visual indicium 73 and an insert feature such as forward user grasp structure 59 may both bear or be colored a first common color, and rear visual indicium 74 and a feature such as rearward user grasp structure 61 may either or both be colored a second common color, visibly distinguishable from the first common color.

In another particular example which may be conceptually appreciated from FIGS. 2I-2J, 2M-2N and 3, front and rear visual indicia 73, 74 disposed on outer cover 20 may embody, or bear images of respective shapes or sizes to match, or cognitively correlate visually correlate with, corresponding shapes or sizes embodied, or pictured on, insert features such as forward and rearward user grasp structures 59, 61 and/or fastener components 56, 57. More particularly, for example, front visual indicium 73 or forward user grasp structure 59 may both embody or bear images of triangles, and rear visual indicium 74 or rearward user grasp structure 61 may both embody or bear images of circles. Other examples of cognitively correlating indicia respectively disposed on an insert and corresponding location on an outer cover include: a baseball and glove, soccer ball and goal, bird and nest, and any other images of components of well-recognized pairings which would indicate to a user that two portions bearing or embodying such images are to be brought together during installation of insert 50 within outer cover 20.

In another particular example, front and rear visual indicia 73, 74 disposed on outer cover 20 may bear images of words or symbolic indications for "front" and "rear", to match corresponding words or symbolic indications on insert features such as forward and rearward user grasp structures 59, 61. In a more particular example, front visual indicium 73 and forward user grasp structure 59 may both bear an image of the letter "F" (i.e., for "front"), and rear visual indicium 74 and rearward user grasp structure 61 may both bear an image of the letter "R" (i.e., for "rear").

In another particular example, front and/or rear visual indicia 73, 74 disposed on outer cover 20 may embody, or bear images of, respective portions of expectedly user-recognizable shapes, characters, objects, etc., to match corresponding portions of expectedly user-recognizable shapes, characters, objects, etc., embodied, or pictured on, insert features such as forward and/or rearward user grasp structures 59, 61. In a more particular example, front visual indicium 73 and forward user grasp structure 59 may both embody or bear respective portions of a first image that, when brought together properly, form a cognitively complete image of an expectedly user-recognizable first shape, character, object, etc.; and/or rear visual indicium 74 and rearward user grasp structure 61 may both embody or bear respective portions of a second image that, when brought together properly, form a cognitively complete image of an expectedly user-recognizable second shape, character, object, etc., distinctive from the first.

In yet another particular example, visual orientation indicia may be simplified into a single pair of visual indicia appearing, respectively, on outer cover 20 and insert 50. In one such example, an inner surface 25 of outer cover 20 may bear an image of an arrow pointing longitudinally toward front edge 21, and insert 50 may bear an image of an arrow pointing longitudinally toward its forward end.

Examples of other suitable visual orientation indicia adapted to provide orientation information may include alphanumeric text including words, arrows, symbols, diagrams, pictographs, icons, cartoons, schematics, and any other visual indicia.

It may be desired that indicia associated with the front portions of the outer cover and insert will not cognitively correlate, or will cognitively not correlate, with indicia associated with rear portions of the outer cover and insert, and vice versa, when the user views both sets of indicia.

From the foregoing it will be appreciated that other forms of visual orientation indicia are possible, within the principle of the foregoing description.

In addition to providing indicia that indicate and/or compel the correct front-rear orientation of the insert with respect to the outer cover, it also may be desirable to provide indicia that indicate and/or compel correct longitudinal and lateral alignment of the insert within the outer cover, in order to provide for the designed optimal containment, fit, comfort and appearance of the article. In the examples shown in FIGS. 2E-2N, respective fastener component pairs 32, 57 and 33, 56 are configured and disposed to serve as alignment indicia. It can be appreciated from these examples that fastener components may be configured and disposed to not only indicate and/or compel correct front/rear orientation, but also indicate and/or compel correct longitudinal and lateral alignment of the insert 50 with respect to the outer cover 20, because co-location of one or both of these fastener component pairs to effect proper fastening will also effect proper longitudinal and lateral alignment. In other examples, separate visual indicia may be included for this purpose, such as, for example, longitudinal alignment indicia 79a, 79b and lateral alignment indicia 78a, 78b disposed respectively on outer cover 20 and insert 50 (FIGS. 2E-2F). Referring to FIGS. 2E-2F, it can be seen that insert 50 may be longitudinally and laterally aligned within outer cover 20 by ensuring that alignment indicia pairs 78a, 78b and 79a, 79b meet, or are closely proximate each other, when insert 50 is installed into outer cover 20. Visual alignment indicia may take other forms, including, but not limited to, matching line segments, shapes, insert end or corner outline images 80 disposed on the inner surfaces of outer cover 20 (see, e.g., FIGS. 2M-2N), etc.

Article of Commerce

It is contemplated that an article of commerce including one or a plurality of outer covers and one or a plurality of inserts, as described herein, may be prepared and sold as such. For example, a package containing from one to 12, or more, outer covers, together with one or a plurality of associated inserts, may be assembled and sold together as packaged. The respective outer cover(s) and inserts in a package may have matching/complementary fastening systems, orientation indicia and/or alignment indicia as described herein.

For such an article of commerce it may be desirable to determine a ratio of inserts to outer covers suitable to constitute a set of convenient numbers of outer covers and inserts, respectively. For example, it may be deemed suitable to include approximately a half day or day's supply of inserts for each outer cover included in the set. Thus, for example, the article of commerce may include inserts and outer covers in a ratio of inserts to outer covers of 1:1, 2:1, 3:1, 4:1, 5:1 or even 6:1. Accordingly, for example, a package associating a set may include one outer cover and 1, 2, 3, 4, 5 or 6 inserts; two outer covers and 2, 4, 6, 8, 10 or 12 inserts; three outer covers and 3, 6, 9, 12, 15 or 18 inserts, and so on. For a "starter" set for certain consumers such as first-time purchasers, or in other circumstances, it may be desirable for a package to contain from 2 to 14 outer covers—which may correspond roughly to from one day's to one week's supply of clean outer covers available before laundering becomes necessary.

It may also be desirable to include, in a set including a plurality of inserts, inserts of differing designs, adapted for use under differing circumstances. In one example, one or more of the inserts in the plurality may be adapted for extended or nighttime use (sleep-use), and one or more for daytime use, with respect to features such as, e.g., location of absorbent material and absorbent capacity. Half of the number of inserts in the plurality, or fewer than half, may be adapted for sleep-use. In one example of this embodiment, the set also may include one or more outer covers decorated with nighttime/sleep themes, such as, for example, images of the moon, stars, nighttime sky colors and other nighttime scenes, images of sleeping animals, sleeping people, sleeping anthropomorphic characters, etc.; and one or more outer covers decorated with daytime/play themes, such as, for example, sun, birds, bright colors, daytime sky colors and other daytime scenes, images of awake/playing animals, people, anthropomorphic characters, etc.

In a further embodiment, a set in a package may be specially adapted for either boys or girls. For example, a package may include one or more outer covers having surface decoration and ornamentation associated with little girls, e.g., inclusion of pink, lavender and/or other soft pastel color schemes, images of flowers, butterflies, bunnies, kittens, little girls, princesses, feminine cartoon characters or feminine anthropomorphic characters, etc., or other decorative features generally associated with little girls. Conversely, a package may include one or more outer covers having decoration and ornamentation associated with little boys, e.g., inclusion of blue, black, dark or bold color schemes, images of cars, trains, planes, boats, rockets, spaceships, objects associated with sports, little boys, masculine cartoon characters or masculine anthropomorphic characters, etc., or other decorative features generally associated with little boys. A package designed for either boys or girls also may include associated corresponding inserts specially adapted for either boys or girls, whether by functional elements or by non-functional, ornamental/decorative elements. Alternatively, a package may contain one or more outer covers and inserts adapted for use with either boys or girls, having gender-neutral decoration/ornamentation and functional elements.

In a further embodiment, a set in a package may include several types of inserts, having functional designs that differ in other respects. For example, a package may include one or more inserts having one or more of a feces acceptance aperture in a topsheet, space beneath the topsheet for isolation of feces, and/or related features such as described in, for example, co-pending U.S. application Ser. Nos. 11/224,779, 11/786,890 and 11/894,087.

In a further embodiment, a set in a package may be specially adapted for use in specific circumstances. For example, a set may include one or more outer covers and associated inserts adapted for wearing while swimming or public bathing. In this example, the outer cover(s) and inserts may be adapted for satisfactory use and to substantially retain structural integrity while soaked and/or immersed in water. For example, the included outer cover(s) may be constructed of materials which do not substantially lose tensile strength, stretch or sag when soaked. In this example, it may be desirable to form the outer covens) predominately of polymeric, hydrophobic materials and/or elasticized textile materials. Similarly, it may be desirable to form included inserts of materials that will withstand immersion and soaking without substantial loss of structural integrity during the period of intended use. It also may be desirable to form such inserts without inclusion of superabsorbent polymer or absorbent gelling material. While these absorbent materials are often included in the absorbent cores of regular diapers, they may be deemed unsuitable for use in articles to be worn while swimming or bathing, because such materials would quickly absorb water, and swell and bulge with the absorbed water, upon being immersed—giving up their absorptive capacity, adding bulk and weight, and retaining no benefit. Within the same set, however, one or more inserts may be included for non-swimming, non-bathing use, such that the same outer cover(s) may be used for swimming/bathing and non-swimming, non-bathing activities. The one or more inserts for non-swimming, non-bathing use may have absorbent cores including superabsorbent polymer or absorbent gelling material.

In a further embodiment, a set in a package may contain a plurality of durable outer covers 20, having leg openings defined by leg opening edges 23 that differ in dimension from one durable outer cover to another durable outer cover. Sequential use of such durable outer covers may be useful to effect a change in the location(s) at which leg band portions 36 and leg opening edges 23 encircle and contact the wearer's skin, each time a durable outer cover in the plurality is replaced by another durable outer cover in the plurality having such differing dimensions. This may provide the advantage of reducing the likelihood or severity of chafing of the wearer's skin in the location(s) of such contact that may result from the wearer's movements. Such chafing may otherwise be caused or exacerbated by repeated use of successive durable outer covers having leg openings of substantially unchanging dimensions, which may result in repeated encircling contact with the skin in a more concentrated or localized fashion. Thus, for example, a user may apply a first durable outer cover in the plurality and the wearer may wear it for a first period of time (such as a day), and the user may apply a second durable outer cover in the plurality and the wearer may wear it for a second period of time (such as the ensuing night or following day), and so on—effectively varying the location(s) on the wearer's skin at which leg opening edges and leg bands encircle and contact it—and reducing the likelihood or severity of chafing. Referring to FIG. 2C, it will be appreciated that varying any of or any combination of, outer cover crotch width $WC_c$, outer cover front width $WC_f$, outer cover rear width $WC_f$, outer cover length LC and leg band length LLB, can have the effect of varying the size of the leg openings of a durable outer cover 20 when applied to the same wearer. Accordingly, a set of at least first and second outer cover in a package may have a difference between them in any of outer cover crotch width $WC_c$, outer cover front width $WC_f$, outer cover rear width $WC_r$, outer cover length LC or leg band length LLB, as measured with each outer cover laid out horizontally on a flat surface, extended to its fullest unstretched (relaxed) dimensions. Any of dimensions $WC_c$, $WC_f$, $WC_r$, LC or LLB may differ between the first and second durable outer covers by at least about 10%, 15%, 20% or more. In another example, however, the tension forces in leg bands 36 may be varied from one durable outer cover to the next, by use of, for example, differing types of elastic strands or strips, or differing sizes of elastic strands or strips, or differing numbers of elastic strands or strips, respectively included by leg band portions 36, or even differing constructions of leg band portions 36—any of which may effect differences in dimensions of leg opening edges 23 from one durable outer cover to another durable outer cover within the package.

In a further embodiment, a variety of packages containing a variety of types of sets may be presented as a variety of articles of commerce. In one example, one or more outer covers forming part of a set in a package may be seasonal in nature, either by reasons of function or decorative/ornamental elements or both. Distinctive sets of outer covers may differ from set to set in attributes such as material basis weight, insulation properties, breathability, etc. For example, a "winter" or "cold weather" outer cover may be formed of materials individually or in combination having a relatively higher basis weight, while a "summer" or "warm weather" outer cover may be formed of relatively lighter materials and/or materials having greater breathability (as may be characterized and compared by WVTR).

In another example, one or more outer covers forming part of a set in a first package may all have decorative/ornamental elements designed by a first designer and/or be labeled or branded with the first designer's name or brand, while one or more outer covers forming part of a set in a second package may all have decorative/ornamental elements designed by a second designer and/or be labeled or branded with the second designer's name or brand. In another example, one or more outer covers forming part of a set in a first package may all have decorative/ornamental elements and/or a label and/or a brand associated with a first particular "collection" or design theme of a designer, while one or more outer covers forming part of a set in a second package may all have decorative/ornamental elements and/or a label and/or a brand associated with a second particular "collection" or design theme of the designer.

In any of the above examples, the outer cover(s) and associated insert(s) in each individual article of commerce will be sized to fit optimally with each other. Thus, in a further example, respective packages may be prepared and presented with sets of outer cover(s) and associated insert(s) distinguished by size. For example, a first package may contain outer cover(s) and associated insert(s) adapted for "size 1" children; a second package may contain outer cover(s) and associated insert(s) adapted for "size 2" children; and so on.

Edge Deflection Force Measurement Method

Figures 6A, 6B:
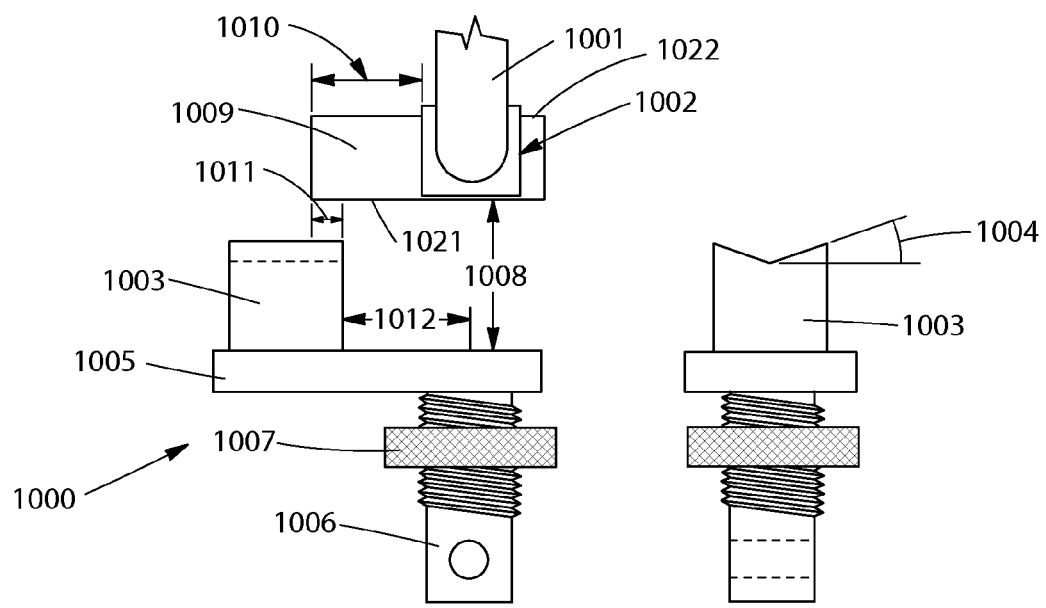
FIG. 6a is a front view of fixtures used on a constant rate of extension tensile tester for use in the Edge Deflection Force Measurement Method herein, with an included test sample.
FIG. 6b is a side view of a lower fixture used on a constant rate of extension tensile tester for use in the Edge Deflection Force Measurement Method herein.

Edge Deflection Force is measured on a constant rate of extension tensile tester with a computer interface (a suitable instrument is the MTS QTest/1 L using Testworks 4.0 software, as available from MTS Systems Corp., Eden Prairie, Minn.) using a load cell for which the forces measured are within 10% to 90% of the limit of the cell. Referring to FIG. 6a, the movable (upper) pneumatic jaws 1001 are fitted with 1 inch×1 inch diamond-faced grips 1002.

The tensile tester is configured for a compression test. Program the tensile tester to lower the crosshead at a rate of 5.0 mm/min until a force of 0.01 N is detected. Zero the time and extension channels and begin data collection at an acquisition rate of 100 Hz. Lower the crosshead at a rate of 50 mm/min for 10 mm and then return the crosshead to its original gage length. From the force versus extension curve, program the software to report the peak force (N).

Referring to FIGS. 6a and 6b, the lower fixture 1000 consists of a base 1005 base 90 mm wide by 40 mm deep by 6 mm thick. The base 1005 is affixed to a suitable mounting device that includes lower mounting shaft 1006, adapted to connect to the stationary mount of the tester. Lower mounting shaft 1006 is threaded as shown and has a locking collar 1007. When the lower mounting shaft 1006 is connected to the stationary mount of the tester, the locking collar 1007 is turned against the stationary mount to immobilize the base 1005 relative the stationary mount of the tester, such that it will remain stationary with the stationary mount, without any interplay therebetween, during testing. Mounted on the base 1005 is a V notched block 1003 that is 30 mm wide by 30 mm deep by 30 mm in height which is made of a low friction material such as Teflon. Referring to the perspective FIG. 6b, the block 1003 is notched from side to center with a "V" at an angle 1004 of 10 degrees. As mounted on the base 1005, the block is centered front to back and offset a distance 1012 of 32.7 mm from the center axis of the mounting shaft 1006, with the line defined by the vertex of the "V" notch intersecting the center axis of the mounting shaft 1006.

Figure 7:
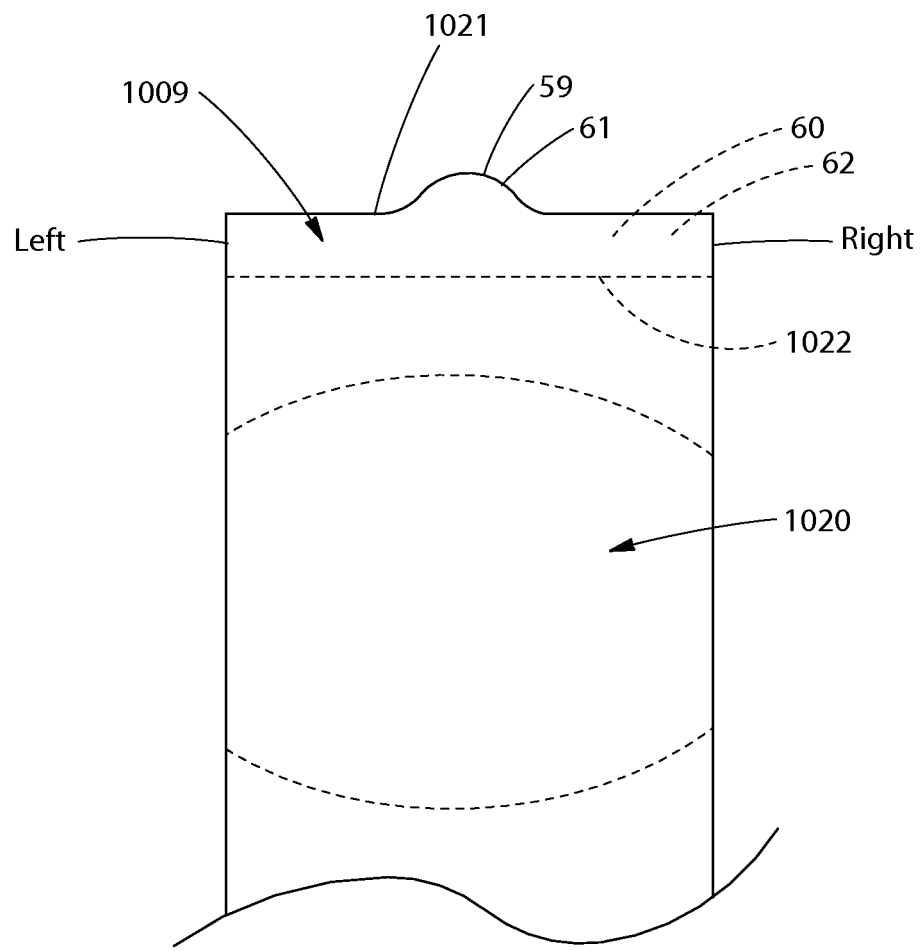
FIG. 7 illustrates preparation of a test sample of an insert including an end support stiffener, for testing in the Edge Deflection Force Measurement Method herein.

Obtain 10 samples from 10 inserts for testing as follows: Determine which of front or rear portions of the inserts are to be tested, and take all 10 samples from such portions accordingly. Lay the insert on a horizontal surface, outer/garment-facing surface up. Referring to FIG. 7: Visually identify the inside edge 1022 of the stiffened portion 1009 of the end (i.e., the portion having end support stiffener 60 or 62). If visually identifying inside edge 1022 is difficult due to the particular construction of the insert, inside edge 1022 may be identified by flattening the insert along the region including the subject end, to its full longitudinal extent (stretching it out against any contraction caused by cuff elastics), laying one hand over the insert near the end to hold the insert in the stretched/flattened position, generally in the location indicated as 1020, and using the other hand to lift outer end edge 1021 vertically. The insert will tend to fold first along inside edge 1022, since a natural "hinge" location will exist at the juncture between the stiffened portion and the adjacent unstiffened portion. Cut the stiffened portion 1009 away from the insert, along edge 1022. Stiffened portion 1009 will now be the sample to be tested. Do not remove any components such as fastener components, grasp structures, etc. If outer edge 1021 is not inherently readily distinguishable from the cut edge by a distinctive feature such as a grasp structure 59, 61, mark outer end edge 1021 for later identification.

All testing is performed in a conditioned room maintained at about 23 C±2 C and about 50%±2% relative humidity. Precondition samples at about 23 C±2 C and about 50%±2% relative humidity for 2 hours prior to testing.

Referring to FIG. 6a for directional and positional orientation, locate a sample 1009 in the grips 1002 with inside edge 1022 horizontal and oriented upward, and outer end edge 1021 oriented downward, and in line with the bottom edges of the grips 1002. Additionally, locate sample 1009 in the grips 1002 such that distance 1010 is 30 mm, and distance 1011 is 10 mm. Close the grips 1002 so that sample 1009 is gripped securely enough so as not to allow it to slip or rotate during testing, but not so tightly as to cause tearing of the sample at the grips during testing.

Zero the load cell and the crosshead position. Start the tensile tester's program, and record the data. Report the peak force (Edge Deflection Force) (N) to ±0.001 N. For each sample, perform the test on both the left and right sides (see FIG. 7), and record the Edge Deflection Force for both sides. Test 10 samples. Calculate the average Edge Deflection Force found of the 10 samples, both sides.

Bending Stiffness Measurement Method

Figure 8:
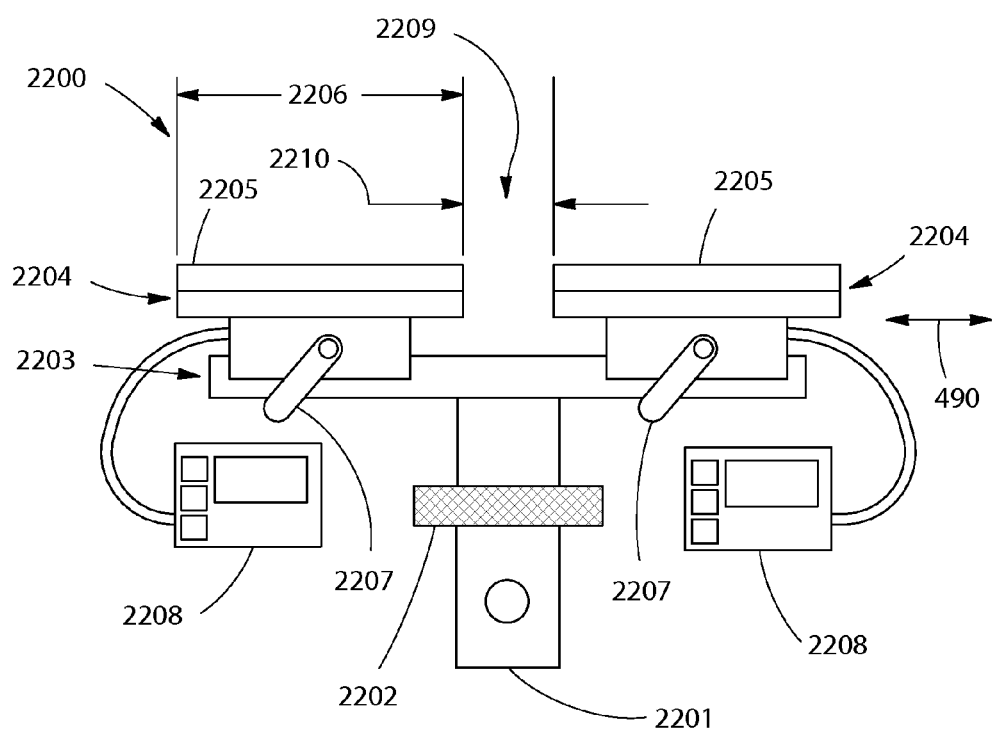
FIG. 8 is a front view of a lower fixture used on a constant rate of extension tensile tester for use in the Bending Stiffness Measurement Method herein.
Figure 9:
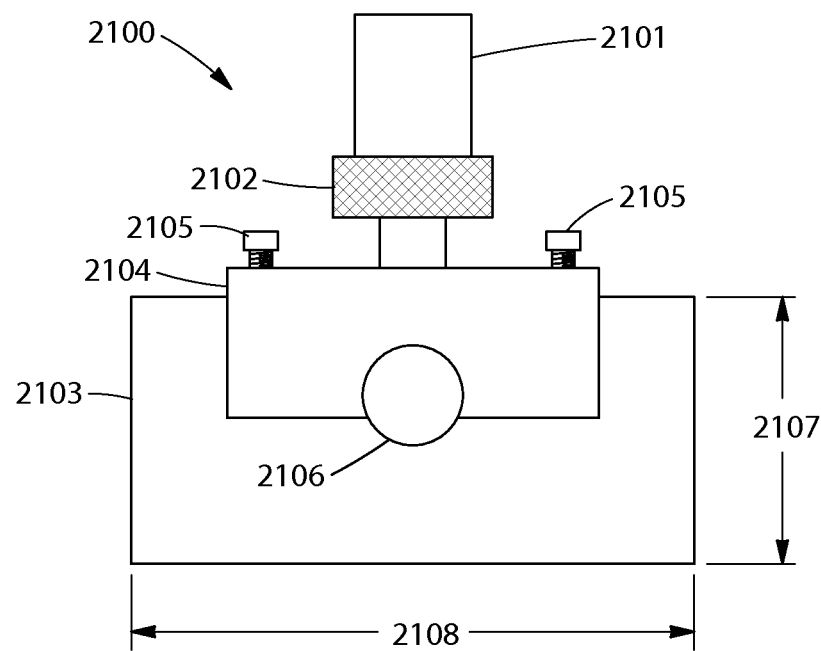
FIG. 9 is a side view of an upper fixture used on a constant rate of extension tensile tester for use in the Bending Stiffness Measurement Method herein.
Figure 10:
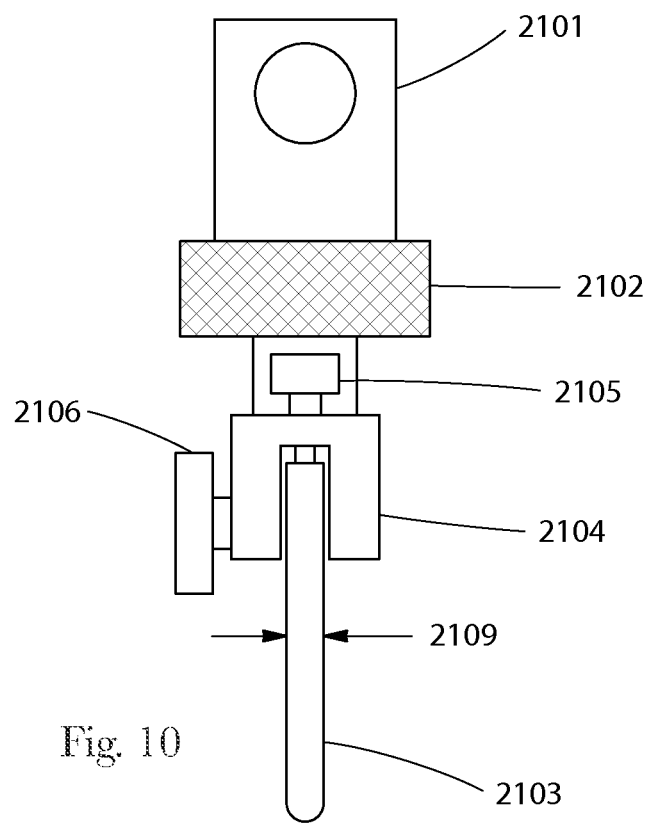
FIG. 10 is a front view of an upper fixture used on a constant rate of extension tensile or use in the Bending Stiffness Measurement Method herein.

Peak Bending Force and Bending Stiffness are measured using a constant rate of extension tensile tester with computer interface (a suitable instrument is an MIS Alliance under TestWorks 4 software, as available from MTS Systems Corp., Eden Prairie, Minn.) fitted with a 10 N load cell. A plunger blade 2100, shown in FIG. 9 (front view) and FIG. 10 (side view), is used for the upper movable test fixture. Base support platforms 2200, shown in FIG. 8, are used as the lower stationary test fixture. All testing is performed in a conditioned room maintained at about 23 C±2 C and about 50%±2% relative humidity.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 25.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm.

Set the crosshead to lower at 500 mm/min for a distance of 25 mm. Set the data acquisition rate to 200 Hz.

Obtain 10 test samples 1009 as described in the description of the Edge Deflection Force Measurement Method, above. (Do not remove any components such as fastener components, grasp structures, etc.) Precondition samples at about 23 C±2 C and about 50%±2% relative humidity for 2 hours prior to testing.

Examine the sample 1009 to be tested for any exposed adhesive and deactivate any exposed adhesive by applying baby powder to it as necessary. Place the sample flat onto the surface of the support platform 2204 over the gap 2209 with the wearer-facing surface facing upward. Center the sample 1009 across the gap, with edge 1022 perpendicular to the gap. Zero the load cell; start the tensile tester and the data acquisition.

Figure 11:
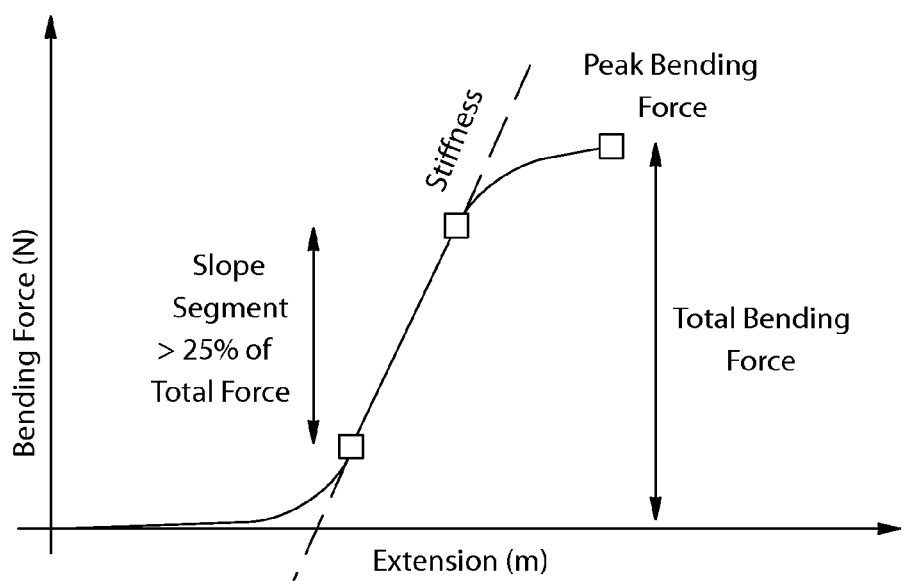
FIG. 11 is a graph showing Peak Bending Force and slope calculation areas on a bending curve.

Program the software to calculate the maximum peak bending force (N) and Stiffness (N/m) from the constructed force (N) verses extension (m) curve. Stiffness is calculated as the slope of the bending force/extension curve for the linear region of the curve (see FIG. 11), using a minimum line segment of at least 25% of the total peak bending force to calculate the slope.

Report Peak Bending Force to the nearest 0.1 N and the Bending Stiffness to the Nearest 0.1 N/m, and record the results. Repeat the test and record the results for all 10 samples. Calculate the average Peak Bending Force and average Bending Stiffness.

A two-piece wearable absorbent article having some or all of the features described herein may provide advantages over both conventional wholly reusable cloth diapers and conventional wholly disposable diapers. The potential for use of semi-durable materials, and more so durable materials, to form an outer cover, provides for an outer cover that may be used more than once, and, depending upon the materials selected, used and laundered many times. An outer cover having some or all of the features described herein may eliminate the necessity for a disposable outer cover structure, thereby reducing the volume of soiled waste the user must dispose of as compared with typical disposable diapers. Additionally, because the possibility of a reusable outer cover that bears most of the structural loading generally imposed upon a disposable diaper is presented, disposable absorbent portions may have more simplified designs, reducing manufacturing and material costs as compared with those of disposable diapers. The possibility for making a disposable absorbent insert of non-traditional renewable materials (such as paper) is presented. At the same time, a disposable absorbent insert and outer cover having some or all of the features described herein may in many circumstances prevent most or all soiling of the outer cover by the wearer's exudates, thereby mitigating sanitation and odor problems associated with handling and storage, reducing the frequency of laundering necessary, and reducing the need for laundering resources, efforts and/or expenses, associated with conventional cloth diapers. A disposable absorbent insert having some or all of the features described herein also may provide better absorbency and better isolation of exudates from both the wearer's skin, and the wearer's clothing and environment, than conventional cloth diapers.

Use of durable materials for an outer cover also may provide other incidental benefits, in creating choices in use of materials for improved and/or more appealing comfort, fit, designs, colors, patterns, etc. as compared with disposable diapers. An outer cover having features described herein provides a wide variety of choices for making a wearable absorbent article look more attractive and/or more like an article of clothing or outerwear. In addition to the foregoing advantages, the use of an insert having an asymmetric structure together with orientation indicia allows for the design of an insert tailored to wearer anatomy and bodily functions as they differ front-to-rear, better performance, and increased economy in design, construction and use of materials, while enabling the user to ensure correct front-rear orientation of the insert within the outer cover. Other advantages are apparent from the description above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended that the appended claims cover all such changes and modifications, and that nothing in the foregoing description or the figures, but rather, only the appended claims, limit the scope of the invention.

What is claimed is:

1. A disposable absorbent insert for use with a reusable outer cover adapted to be worn about a wearer's lower torso, the insert having a longitudinal length, a central longitudinal axis, an insert forward region, an insert rearward region, and an insert lateral axis between the insert forward and rearward regions and equally dividing the longitudinal length, comprising an insert indicium disposed thereon;
   wherein the insert is asymmetric across the insert lateral axis, and is adapted to function on and/or fit the wearer optimally with the insert forward region disposed proximate to a torso front region of the wearer's lower torso and the insert rearward region disposed proximate to a torso rear region of the wearer's lower torso;
   wherein the insert indicium provides information to a user concerning correct front-rear orientation of the insert with respect to the reusable outer cover or the wearer;
   wherein the insert is asymmetric about the insert lateral axis by having a different weight of superabsorbent polymer or absorbent gelling material present across the insert lateral axis;
   wherein the insert comprises a user grasp structure extending from an end edge of the insert forward region or an end edge of the insert rearward region, wherein the user grasp structure defines an aperture therein;
   a first fastener component in the insert forward region and on a first side of the central longitudinal axis;
   a second fastener component in the insert forward region and on a second side of the central longitudinal axis and oppositely disposed about the central longitudinal axis with respect to the first fastener component; and
   a third fastener component in the insert rearward region and intersecting the central longitudinal axis.

2. The insert of claim 1 comprising a pair of elasticized standing cuffs.

3. The insert of claim 2 comprising an end support stiffener in the insert rearward region.

4. The insert of claim 3 comprising a liquid permeable topsheet, a substantially liquid impervious backsheet, and an absorbent core disposed between the topsheet and the backsheet.

5. The insert of claim 4 wherein the absorbent core comprises a layer comprising distributed particles of superabsorbent polymer or absorbent gelling material captured by a thermoplastic adhesive composition.

6. The insert of claim 4 wherein the backsheet is formed of a vapor permeable material.

7. The insert of claim 6 wherein the standing cuffs are formed of a vapor permeable material.

8. The insert of claim 1 wherein the insert indicium is visual or tactile.

9. The insert of claim 1 wherein the insert is asymmetric about the insert lateral axis by having a difference across the insert lateral axis selected from the group consisting of weight, absorbent capacity, wearer-facing surface area, lateral width, and combinations thereof.

10. A disposable absorbent insert for use with a reusable outer cover forming a portion of a diaper and configured to be worn about a wearer's lower torso, the insert having a longitudinal length and a central longitudinal axis, an insert forward region, an insert rearward region, and an insert lateral axis between the forward and rearward regions and equally dividing the longitudinal length, comprising an insert indicium disposed thereon;
   wherein the insert is asymmetric across the insert lateral axis, and is adapted to function on and/or fit the wearer optimally with the insert forward region disposed proximate to a torso front region of the wearer's lower torso and the insert rearward region disposed proximate to a torso rear region of the wearer's lower torso;
   wherein the insert indicium provides information to a user concerning correct front-rear orientation of the insert with respect to the reusable outer cover or the wearer;
   wherein the insert is asymmetric about the insert lateral axis by having a different weight across the insert lateral axis; and
   a first fastener component in the insert forward region and on a first side of the central longitudinal axis;
   a second fastener component in the insert forward region and on a second side of the central longitudinal axis and oppositely disposed about the central longitudinal axis with respect to the first fastener component; and
   a third fastener component in the insert rearward region and overlapping the central longitudinal axis.

11. The insert of claim 10 comprising a pair of elasticized standing cuffs.

12. The insert of claim 11 comprising an end support stiffener in the insert rearward region.

13. The insert of claim 12 comprising a liquid permeable topsheet, a substantially liquid impervious backsheet formed of a vapor permeable material, and an absorbent core disposed between the topsheet and the backsheet.

14. The insert of claim 13 wherein the absorbent core comprises a layer comprising distributed particles of superabsorbent polymer or absorbent gelling material captured by a thermoplastic adhesive composition.

15. A disposable absorbent insert for use with a reusable outer cover forming a portion of a taped diaper and configured to be worn about a wearer's lower torso, the insert having a longitudinal length, a central longitudinal axis, an insert forward region, an insert rearward region, and an insert lateral axis between the forward and rearward regions and equally dividing the longitudinal length, comprising an insert indicium disposed thereon;

wherein the insert is asymmetric across the insert lateral axis, and is adapted to function on and/or fit the wearer optimally with the insert forward region disposed proximate to a torso front region of the wearer's lower torso and the insert rearward region disposed proximate to a torso rear region of the wearer's lower torso;

wherein the insert indicium provides information to a user concerning correct front-rear orientation of the insert with respect to the reusable outer cover or the wearer;

wherein the insert is asymmetric about the insert lateral axis by having a different absorbent capacity across the insert lateral axis;

wherein the insert comprises a first user grasp structure extending from an end edge of the insert forward region and a second user grasp structure in the insert rearward region, and wherein the first user grasp structure comprises an aperture as the insert indicium;

a first fastener component in the insert forward region and on a first side of the central longitudinal axis;

a second fastener component in the insert forward region and on a second side of the central longitudinal axis and oppositely disposed about the central longitudinal axis with respect to the first fastener component; and a third fastener component in the insert rearward region and intersecting and overlapping the central longitudinal axis.

16. The insert of claim 15, wherein the insert comprises a liquid permeable topsheet, a substantially liquid impervious backsheet formed of a vapor permeable material, and an absorbent core disposed between the topsheet and the backsheet, and wherein the absorbent core comprises a layer comprising distributed particles of superabsorbent polymer or absorbent gelling material captured by a thermoplastic adhesive composition.

* * * * *